(12) United States Patent
Basu et al.

(10) Patent No.: US 8,946,312 B2
(45) Date of Patent: Feb. 3, 2015

(54) AZEOTROPE-LIKE COMPOSITIONS COMPRISING 1-CHLORO-3,3,3-TRIFLUOROPROPENE

(75) Inventors: Rajat Basu, East Amherst, NY (US); Leslie Bement, Buffalo, NY (US); Kane Cook, Egertsville, NY (US); Ryan Hulse, Getzville, NY (US); Gary Knopeck, Lakeview, NY (US); Hang T. Pham, Amherst, NY (US); Rajiv R. Singh, Getzville, NY (US); David J. Williams, East Amherst, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 13/298,471

(22) Filed: Nov. 17, 2011

(65) Prior Publication Data

US 2012/0064014 A1    Mar. 15, 2012

Related U.S. Application Data

(63) Continuation of application No. 12/605,609, filed on Oct. 26, 2009, now Pat. No. 8,163,196, which is a continuation-in-part of application No. 12/259,694, filed on Oct. 28, 2008, now Pat. No. 7,935,268.

(60) Provisional application No. 61/109,007, filed on Oct. 28, 2008.

(51) Int. Cl.

| | |
|---|---|
| *C08J 9/06* | (2006.01) |
| *C09K 5/04* | (2006.01) |
| *C08J 9/12* | (2006.01) |
| *C08J 9/14* | (2006.01) |
| *C09K 3/30* | (2006.01) |
| *C11D 7/26* | (2006.01) |
| *C11D 7/50* | (2006.01) |
| *C11D 7/28* | (2006.01) |

(52) U.S. Cl.
CPC .............. *C09K 5/044* (2013.01); *C08J 9/127* (2013.01); *C08J 9/149* (2013.01); *C09K 3/30* (2013.01); *C11D 7/261* (2013.01); *C11D 7/5081* (2013.01); *C08J 2203/06* (2013.01); *C08J 2203/12* (2013.01); *C08J 2203/14* (2013.01); *C08J 2203/142* (2013.01); *C08J 2205/052* (2013.01); *C08J 2375/04* (2013.01); *C11D 7/28* (2013.01)
USPC .............. 521/131; 521/134; 252/67; 264/53

(58) Field of Classification Search
USPC ............. 521/131, 134; 252/67; 264/53
See application file for complete search history.

(56) References Cited

U.S. PATENT DOCUMENTS

| | | |
|---|---|---|
| 2,739,987 A | 3/1956 | Ruh |
| 2,834,748 A | 5/1958 | Bailey et al. |
| 2,846,458 A | 8/1958 | Haluska |
| 2,889,379 A | 6/1959 | Ruh et al. |
| 2,917,480 A | 12/1959 | Bailey et al. |
| 4,465,786 A | 8/1984 | Zimmer et al. |
| 4,798,818 A | 1/1989 | Baizer et al. |
| 4,960,535 A | 10/1990 | Logsdon et al. |
| 4,961,870 A | 10/1990 | Cook et al. |
| 6,380,275 B1 * | 4/2002 | Kruecke et al. ............. 521/131 |
| 7,438,825 B1 | 10/2008 | Chen et al. |
| 7,442,321 B1 | 10/2008 | Chen et al. |
| 7,935,268 B2 | 5/2011 | Basu et al. |
| 2004/0192796 A1 * | 9/2004 | Gensous et al. ............. 521/155 |
| 2007/0105738 A1 | 5/2007 | Nappa et al. |
| 2007/0112231 A1 | 5/2007 | Wilmet et al. |
| 2008/0011678 A1 | 1/2008 | Knapp |
| 2008/0313985 A1 | 12/2008 | Duncan |
| 2009/0253820 A1 | 10/2009 | Bowman et al. |
| 2009/0305876 A1 | 12/2009 | Singh et al. |
| 2010/0102273 A1 | 4/2010 | Basu et al. |
| 2010/0113629 A1 * | 5/2010 | Van Horn et al. ............. 521/98 |
| 2011/0041529 A1 | 2/2011 | Chen et al. |

FOREIGN PATENT DOCUMENTS

| | | |
|---|---|---|
| EP | 0974571 A2 | 1/2000 |
| WO | 2008/121776 A1 | 10/2008 |

OTHER PUBLICATIONS

PCT International Search Report—PCT/US2009/062146, Filed Oct. 27, 2009 (WO).
M.S. Kim et al, "A Study to Determine Existence of an Azeotropic R-22 Drop-In Substitute," NISTIR 5784, National Institute of Standards and Technology, Mar. 1996 U.S.
Kim, et al., "A Study to Determine the Existence of an Azeotropic R-22 "Drop-In" Substitute," prepared by U.S. Department of Commerce for Electric Power Research Institute, Mar. 1996, pp. 1-45, U.S.
Morrison, et al., "Azeotropy in Refrigerant Mixtures," International Journal of Refrigeration, 1993, pp. 129-138, vol. 16, No. 2. U.S.

* cited by examiner

*Primary Examiner* — John Hardee
(74) *Attorney, Agent, or Firm* — Colleen D. Szuch

(57) ABSTRACT

An azeotrope-like mixture consisting essentially of chlorotrifluoropropene and at least one component selected from the group consisting of a $C_1$-$C_3$ alcohol, a $C_5$-$C_6$ hydrocarbon, a halogenated hydrocarbon, methylal, methyl acetone, water, nitromethane, and combinations thereof.

15 Claims, No Drawings

AZEOTROPE-LIKE COMPOSITIONS COMPRISING 1-CHLORO-3,3,3-TRIFLUOROPROPENE

CROSS-REFERENCE TO RELATED APPLICATIONS

This application is a continuation of U.S. application Ser. No. 12/605,609, filed Oct. 26, 2009, now U.S. Pat. No. 8,163,196 which claims the priority benefit of U.S. Provisional Application No. 61/109,007, filed Oct. 28, 2008, and which is also a continuation-in-part (CIP) of U.S. application Ser. No. 12/259,694, filed Oct. 28, 2008, now U.S. Pat. No. 7,935,268 the contents each of which are incorporated herein by reference in its entirety.

BACKGROUND

1. Field of Invention

The present invention relates generally to compositions comprising 1-chloro-3,3,3-trifluoropropene. More specifically, the present invention provides azeotrope-like compositions comprising 1-chloro-3,3,3-trifluoropropene and uses thereof.

2. Description of Related Art

Fluorocarbon based fluids, including chlorofluorocarbons ("CFCs") or hydrochlorofluorocarbons ("HCFCs"), have properties that are desirable in industrial refrigerants, blowing agents, heat transfer media, solvents, gaseous dielectrics, and other applications. For these applications, the use of single component fluids or azeotrope-like mixtures, i.e., those which do not substantially fractionate on boiling and evaporation, are particularly desirable.

Unfortunately, suspected environmental problems, such as global warming and ozone depletion, have been attributed to the use of some of these fluids, thereby limiting their contemporary use. Hydrofluoroolefins ("HFOs") have been proposed as possible replacements for such CFCs, HCFCs, and HFCs. However, the identification of new, environmentally-safe, non-fractionating mixtures comprising HFOs are complicated due to the fact that azeotrope formation is not readily predictable. Therefore, industry is continually seeking new HFO-based mixtures that are acceptable and environmentally safer substitutes for CFCs, HCFCs, and HFCs. This invention satisfies these needs among others.

SUMMARY OF INVENTION

Applicants have discovered that azeotrope-like compositions are formed upon mixing 1-chloro-3,3,3-trifluoropropene ("HFO-1233zd") with a second component selected from the group consisting of a $C_1$-$C_3$ alcohol, a $C_5$-$C_6$ hydrocarbon, cyclopentene, a halogenated hydrocarbon selected from 1-chloropropane, 2-chloropropane, and 1,1,1,3,3-pentafluorobutane, water and optionally nitromethane. Preferred azeotrope-like mixtures of the invention exhibit characteristics which make them particularly desirable for number of applications, including as refrigerants, as blowing agents in the manufacture of insulating foams, and as solvents in a number of cleaning and other applications, including in aerosols and other sprayable compositions. In particular, applicants have recognized that these compositions tend to exhibit relatively low global warming potentials ("GWPs"), preferably less than about 1000, more preferably less than about 500, and even more preferably less than about 150.

Accordingly, one aspect of the present invention involves a composition comprising a binary azeotrope-like mixture consisting essentially of 1-chloro-3,3,3-trifluoropropene and a second component selected from the group consisting of a $C_1$-$C_3$ alcohol, a $C_5$-$C_6$ hydrocarbon, cyclopentene, a halogenated hydrocarbon selected from 1-chloropropane, 2-chloropropane, and 1,1,1,3,3-pentafluorobutane, water and optionally nitromethane. In certain preferred embodiments, the composition further comprises one or more of the following: co-blowing agent, co-solvent, active ingredient, and additive such as lubricants, stabilizers, metal passivators, corrosion inhibitors, and flammability suppressants. In certain preferred embodiments, nitromethane is included in the mixture as a stabilizer. In certain embodiments, nitromethane also contributes to the azeotrope-like properties of the composition.

Another aspect of the invention provides a blowing agent comprising at least about 15 wt. % of an azeotrope-like mixture as described herein, and, optionally, co-blowing agents, fillers, vapor pressure modifiers, flame suppressants, and stabilizers.

Another aspect of the invention provides a solvent for use in vapor degreasing, cold cleaning, wiping and similar solvent applications comprising an azeotrope-like mixture as described herein.

Another aspect of the invention provides a sprayable composition comprising an azeotrope-like mixture as described herein, an active ingredient, and, optionally, inert ingredients and/or solvents and aerosol propellants.

Yet another aspect of the invention provides closed cell foam comprising a polyurethane-, polyisocyanurate-, or phenolic-based cell wall and a cell gas disposed within at least a portion of the cell wall structure, wherein the cell gas comprises the azeotrope-like mixture as described herein.

According to another embodiment, provided is a polyol premix comprising the azeotrope-like mixture described herein.

According to another embodiment, provided is a foamable composition comprising the azeotrope-like mixture described herein.

According to another embodiment, provided is a method for producing thermoset foam comprising (a) adding a blowing agent comprising an azeotrope-like composition according to claim 1 to a foamable mixture comprising a thermosetting resin; (b) reacting said foamable mixture to produce a thermoset foam; and (c) volatilizing said azeotrope-like composition during said reacting.

According to another embodiment, provided is a method for producing thermoplastic foam comprising (a) adding a blowing agent comprising an azeotrope-like composition according to claim 1 to a foamable mixture comprising a thermoplastic resin; (b) reacting said foamable mixture to produce a thermoplastic foam; and (c) volatilizing said azeotrope-like composition during said reacting.

According to another embodiment, provided is a thermoplastic foam having a cell wall comprising a thermoplastic polymer and a cell gas comprising an azeotrope-like mixture as described herein. Preferably, the thermoplastic foam comprises a cell gas having an azeotrope-like mixture as described herein and having a cell wall constructed of a thermoplastic polymer selected from polystyrene, polyethylene, polypropylene, polyvinyl chloride, polytheyeneterephthalate or combinations thereof.

According to another embodiment, provided is a thermoset foam having a cell wall comprising a thermosetting polymer and a cell gas comprising an azeotrope-like mixture as described herein. Preferably, the thermoset foam comprises a cell gas having an azeotrope-like mixture as described herein and a cell wall comprising a thermoset polymer selected from polyurethane, polyisocyanurate, phenolic, epoxy, or combinations thereof.

According to another embodiment of the invention, provided is a refrigerant comprising an azeotrope-like mixture as described herein.

DESCRIPTION OF PREFERRED EMBODIMENTS

According to certain embodiments, the present invention provides azeotrope-like compositions comprising, and preferably consisting essentially of, HFO-1233zd and a $C_1$-$C_3$ alcohol, a $C_5$-$C_6$ hydrocarbon, cyclopentene, a halogenated hydrocarbon selected from 1-chloropropane, 2-chloropropane, and 1,1,1,3,3-pentafluorobutane, nitromethane, or water. Thus, the present invention overcomes the aforementioned shortcomings by providing azeotrope-like compositions that are, in preferred embodiments, substantially free of CFCs, HCFCs, and HFCs and have very low global warming potentials have low ozone depletion potential, and which exhibit relatively constant boiling point characteristics.

As used herein, the term "azeotrope-like" relates to compositions that are strictly azeotropic or that generally behave like azeotropic mixtures. An azeotropic mixture is a system of two or more components in which the liquid composition and vapor composition are equal at the stated pressure and temperature. In practice, this means that the components of an azeotropic mixture are constant-boiling or essentially constant-boiling and generally cannot be thermodynamically separated during a phase change. The vapor composition formed by boiling or evaporation of an azeotropic mixture is identical, or substantially identical, to the original liquid composition. Thus, the concentration of components in the liquid and vapor phases of azeotrope-like compositions change only minimally, if at all, as the composition boils or otherwise evaporates. In contrast, boiling or evaporating non-azeotropic mixtures changes the component concentrations in the liquid phase to a significant degree.

As used herein, the term "consisting essentially of", with respect to the components of an azeotrope-like composition, means the composition contains the indicated components in an azeotrope-like ratio, and may contain additional components provided that the additional components do not form new azeotrope-like systems. For example, azeotrope-like mixtures consisting essentially of two compounds are those that form binary azeotropes, which optionally may include one or more additional components, provided that the additional components do not render the mixture non-azeotropic and do not form an azeotrope with either or both of the compounds.

The term "effective amounts" as used herein refers to the amount of each component which, upon combination with the other component, results in the formation of an azeotrope-like composition of the present invention.

Unless otherwise specified, the term HFO-1233zd means the cis-isomer, the trans-isomer, or some mixture thereof.

As used herein, the term cis-HFO-1233zd with respect to a component of an azeotrope-like mixture, means the amount cis-HFO-1233zd relative to all isomers of HFO-1233zd in azeotrope-like compositions is at least about 95%, more preferably at least about 98%, even more preferably at least about 99%, even more preferably at least about 99.9%. In certain preferred embodiments, the cis-HFO-1233zd component in azeotrope-like compositions of the present invention is essentially pure cis-HFO-1233zd.

As used herein, the term trans-HFO-1233zd with respect to a component of an azeotrope-like mixture, means the amount trans-HFO-1233zd relative to all isomers of HFO-1233zd in azeotrope-like compositions is at least about 95%, more preferably at least about 98%, even more preferably at least about 99%, even more preferably at least about 99.9%. In certain preferred embodiments, the trans-HFO-1233zd component in azeotrope-like compositions of the present invention is essentially pure trans-HFO-1233zd.

As used herein, the term "ambient pressure" with respect to boiling point data means the atmospheric pressure surrounding the relevant medium. In general, ambient pressure is 14.7 psia, but could vary +/−0.5 psi.

The azeotrope-like compositions of the present invention can be produced by combining effective amounts of HFO-1233zd with one or more other components, preferably in fluid form. Any of a wide variety of methods known in the art for combining two or more components to form a composition can be adapted for use in the present methods. For example, HFO-1233zd and methanol can be mixed, blended, or otherwise combined by hand and/or by machine, as part of a batch or continuous reaction and/or process, or via combinations of two or more such steps. In light of the disclosure herein, those of skill in the art will be readily able to prepare azeotrope-like compositions according to the present invention without undue experimentation.

Fluoropropenes, such as $CF_3CCl=CH_2$, can be produced by known methods such as catalytic vapor phase fluorination of various saturated and unsaturated halogen-containing C3 compounds, including the method described in U.S. Pat. Nos. 2,889,379; 4,798,818 and 4,465,786, each of which is incorporated herein by reference.

EP 974,571, also incorporated herein by reference, discloses the preparation of 1,1,1,3-chlorotrifluoropropene by contacting 1,1,1,3,3-pentafluoropropane (HFC-245fa) in the vapor phase with a chromium based catalyst at elevated temperature, or in the liquid phase with an alcoholic solution of KOH, NaOH, $Ca(OH)_2$ or $Mg(OH)_2$. The end product is approximately 90% by weight of the trans isomer and 10% by weight cis. Preferably, the cis isomers are substantially separated from the trans forms so that the resultant preferred form of 1-chloro-3,3,3-trifluoropropene is more enriched in the cis isomer. Because the cis isomer has a boiling point of about 40° C. in contrast with the trans isomer boiling point of about 20° C., the two can easily be separated by any number of distillation methods known in the art. However, a preferred method is batch distillation. According to this method, a mixture of cis and trans 1-chloro-3,3,3-trifluoropropene is charged to the reboiler. The trans isomer is removed in the overhead leaving the cis isomer in the reboiler. The distillation can also be run in a continuous distillation where the trans isomer is removed in the overhead and the cis isomer is removed in the bottom. This distillation process can yield about 99.9+% pure trans-1-chloro-3,3,3-trifluoropropene and 99.9+% cis-1-chloro-3,3,3-trifluoropropene.

In a preferred embodiments, the azeotrope-like composition comprises effective amounts of HFO-1233zd and a $C_1$-$C_3$ alcohol. Preferably, the $C_1$-$C_3$ alcohol is selected from the group consisting of methanol, ethanol, and isopropanol. In certain preferred embodiments, the HFO-1233zd is trans-HFO-1233zd. In certain other embodiments, the HFO-1233zd is cis-HFO-1233zd.

Cis-HFO-1233Zd/Methanol Azeotrope-Like Compositions:

In a preferred embodiment, the azeotrope-like composition comprises effective amounts of cis-HFO-1233zd and methanol. More preferably, these binary azeotrope-like compositions consist essentially of about 78 to about 99.9 wt. % cis-HFO-1233zd and from about 0.1 to about 22 wt. % methanol, more preferably from about 85 to about 99.9 wt. % cis-HFO-1233zd and about 0.1 to about 15 wt. % methanol, and even more preferably from about 88 to about 99.5 wt. % cis-HFO-1233zd and from about 0.5 to about 12 wt. % methanol.

Preferably, the cis-HFO-1233zd/methanol compositions of the present invention have a boiling point of about 35.2±1° C. at ambient pressure (Ambient pressure need to be defined)

Trans-HFO-1233zd/Methanol Azeotrope-Like Compositions:

In a preferred embodiment, the azeotrope-like composition comprises effective amounts of trans-HFO-1233zd and methanol. More preferably, these binary azeotrope-like compositions consist essentially of about 70 to about 99.95 wt. % trans-HFO-1233zd and from about 0.05 to about 30 wt. % methanol, more preferably from about 90 to about 99.95 wt. % trans-HFO-1233zd and about 0.05 to about 10 wt. % methanol, and even more preferably from about 95 to about 99.95 wt. % trans-HFO-1233zd and from about 0.05 to about 5 wt. % methanol.

Preferably, the trans-HFO-1233zd/methanol compositions of the present invention have a boiling point of from about 17° C. to about 19° C., more preferably about 17° C. to about 18° C., even more preferably about 17° C. to about 17.5° C., and most preferably about 17.15° C.±1° C., all measured at ambient pressure.

Cis-HFO-1233zd/Ethanol Azeotrope-Like Compositions:

In a preferred embodiment, the azeotrope-like composition comprises effective amounts of cis-HFO-1233zd and ethanol. More preferably, these binary azeotrope-like compositions consist essentially of about 65 to about 99.9 wt. % cis-HFO-1233zd and from about 0.1 to about 35 wt. % ethanol, more preferably from about 79 to about 99.9 wt. % cis-HFO-1233zd and about 0.1 to about 21 wt. % ethanol, and even more preferably from about 88 to about 99.5 wt. % cis-HFO-1233zd and from about 0.5 to about 12 wt. % ethanol.

Preferably, the cis-HFO-1233zd/ethanol compositions of the present invention have a normal boiling point of about 37.4° C.±1° C. at ambient pressure.

Trans-HFO-1233zd/Ethanol Azeotrope-Like Compositions:

In a preferred embodiment, the azeotrope-like composition comprises effective amounts of trans-HFO-1233zd and ethanol. More preferably, these binary azeotrope-like compositions consist essentially of about 85 to about 99.9 wt. % trans-HFO-1233zd and from about 0.1 to about 15 wt. % ethanol, more preferably from about 92 to about 99.9 wt. % trans-HFO-1233zd and about 0.1 to about 8 wt. % ethanol, and even more preferably from about 96 to about 99.9 wt. % trans-HFO-1233zd and from about 0.1 to about 4 wt. % ethanol.

Preferably, the trans-HFO-1233zd/ethanol compositions of the present invention have a normal boiling point of about 18.1° C.±1° C. at ambient pressure.

Cis-HFO-1233zd/Isopropanol Azeotrope-Like Compositions:

In a preferred embodiment, the azeotrope-like composition comprises effective amounts of cis-HFO-1233zd and isopropanol. More preferably, these binary azeotrope-like compositions consist essentially of about 85 to about 99.99 wt. % cis-HFO-1233zd and from about 0.01 to about 15 wt. % isopropanol, more preferably from about 88 to about 99.99 wt. % cis-HFO-1233zd and about 0.01 to about 12 wt. % isopropanol, and even more preferably from about 92 to about 99.5 wt. % cis-HFO-1233zd and from about 0.5 to about 8 wt. % isopropanol.

Preferably, the cis-HFO-1233zd/isopropanol compositions of the present invention have a normal boiling point of about 38.1° C.±1° C. at ambient pressure.

Trans-HFO-1233zd/Isopropanol Azeotrope-Like Compositions:

In a preferred embodiment, the azeotrope-like composition comprises effective amounts of trans-HFO-1233zd and isopropanol. More preferably, these binary azeotrope-like compositions consist essentially of about 90 to about 99.9 wt. % trans-HFO-1233zd and from about 0.1 to about 10 wt. % isopropanol, more preferably from about 94 to about 99.9 wt. % trans-HFO-1233zd and about 0.1 to about 6 wt. % isopropanol, and even more preferably from about 95 to about 99.9 wt. % trans-HFO-1233zd and from about 0.1 to about 5 wt. % isopropanol.

Preferably, the trans-HFO-1233zd/isopropanol compositions of the present invention have a normal boiling point of about 17.9° C.±1° C. at ambient pressure.

In a preferred embodiments, the azeotrope-like composition comprises effective amounts of HFO-1233zd and a $C_5$-$C_6$ hydrocarbon. Preferably, the $C_5$-$C_6$ hydrocarbon is selected from the group consisting of n-pentane, isopentane, neopentane, cyclopentane, cyclopentene, n-hexane, and isohexane. In certain preferred embodiments, the HFO-1233zd is trans-HFO-1233zd. In certain other embodiments, the HFO-1233zd is cis-HFO-1233zd.

Trans-HFO-1233zd/n-Pentane Azeotrope-Like Compositions:

In a preferred embodiment, the azeotrope-like composition comprises effective amounts of trans-HFO-1233zd and n-pentane. More preferably, these binary azeotrope-like compositions consist essentially of about 65 to about 99.95 wt. % trans-HFO-1233zd and from about 0.05 to about 35 wt. % n-pentane, more preferably from about 84 to about 99.9 wt. % trans-HFO-1233zd and about 0.1 to about 16 wt. % n-pentane, and even more preferably from about 92 to about 99.5 wt. % trans-HFO-1233zd and from about 0.5 to about 8 wt. % n-pentane.

Preferably, the trans-HFO-1233zd/n-pentane compositions of the present invention have a boiling point of from about 17° C. to about 19° C., more preferably about 17° C. to about 18° C., even more preferably about 17.3° C. to about 17.6° C., and most preferably about 17.4° C.±1° C., all measured at ambient pressure.

Cis-HFO-1233zd/n-Pentane Azeotrope-Like Compositions:

In a preferred embodiment, the azeotrope-like composition comprises effective amounts of cis-HFO-1233zd and n-pentane. More preferably, these binary azeotrope-like compositions consist essentially of about 20 to about 99.5 wt. % cis-HFO-1233zd and from about 0.5 to about 80 wt. % n-pentane, more preferably from about 50 to about 99.5 wt. % cis-HFO-1233zd and about 0.5 to about 50 wt. % n-pentane, and even more preferably from about 60 to about 99.5 wt. % cis-HFO-1233zd and from about 0.5 to about 40 wt. % n-pentane.

Preferably, the cis-HFO-1233zd/n-pentane compositions of the present invention have a normal boiling point of about 35° C.±1° C. at ambient pressure.

Trans-HFO-1233zd/Isopentane Azeotrope-Like Compositions:

In a preferred embodiment, the azeotrope-like composition comprises effective amounts of trans-HFO-1233zd and isopentane. More preferably, these binary azeotrope-like compositions consist essentially of about 60 to about 99.95 wt. % trans-HFO-1233zd and from about 0.05 to about 40 wt. % isopentane, more preferably from about 70 to about 95 wt. % trans-HFO-1233zd and about 5 to about 30 wt. % isopentane, and even more preferably from about 80 to about 90 wt. % trans-HFO-1233zd and from about 10 to about 20 wt. % isopentane.

Preferably, the trans-HFO-1233zd/isopentane compositions of the present invention have a boiling of from about 15° C. to about 18° C., more preferably about 16° C. to about 17° C., even more preferably about 16.7° C. to about 16.9° C., and most preferably about 16.8° C.±1° C., all measured at ambient pressure.

Trans-HFO-1233zd/Neopentane Azeotrope-Like Compositions:

In a preferred embodiment, the azeotrope-like composition comprises effective amounts of trans-HFO-1233zd and neopentane. More preferably, these binary azeotrope-like compositions consist essentially of about 5 to about 70 wt. % trans-HFO-1233zd and from about 30 to about 95 wt. % neopentane, more preferably from about 15 to about 55 wt. % trans-HFO-1233zd and about 45 to about 85 wt. % neopentane, and even more preferably from about 20 to about 50 wt. % trans-HFO-1233zd and from about 50 to about 80 wt. % neopentane.

Preferably, the trans-HFO-1233zd/neopentane compositions of the present invention have a boiling of from about 7.7° C. to about 8.4° C., more preferably about 7.7° C. to about 8.0° C., and most preferably about 7.7° C.±1° C., all measured at ambient pressure.

Cis-HFO-1233zd/Neopentane Azeotrope-Like Compositions:

In a preferred embodiment, the azeotrope-like composition comprises effective amounts of cis-HFO-1233zd and neopentane. More preferably, these binary azeotrope-like compositions consist essentially of about 5 to about 50 wt. % cis-HFO-1233zd and from about 50 to about 95 wt. % neopentane, more preferably from about 20 to about 45 wt. % cis-HFO-1233zd and about 55 to about 80 wt. % neopentane, and even more preferably from about 30 to about 40 wt. % cis-HFO-1233zd and from about 60 to about 70 wt. % neopentane.

Preferably, the cis-HFO-1233zd/neopentane compositions of the present invention have a normal boiling point of about 8° C.±1° C.

Trans-HFO-1233zd/Cyclopentane Azeotrope-Like Compositions:

In a preferred embodiment, the azeotrope-like composition comprises effective amounts of trans-HFO-1233zd and cyclopentane. More preferably, these binary azeotrope-like compositions consist essentially of about 95 to about 99.9 wt. % trans-HFO-1233zd and from about 0.1 to about 5 wt. % cyclopentane, more preferably from about 97 to about 99.9 wt. % trans-HFO-1233zd and about 0.1 to about 3 wt. % cyclopentane, and even more preferably from about 98 to about 99.9 wt. % trans-HFO-1233zd and from about 2 to about 98 wt. % cyclopentane.

Preferably, the trans-HFO-1233zd/cyclopentane compositions of the present invention have a normal boiling point of about 17.5° C.±1° C. at ambient pressure.

Cis-HFO-1233zd/Cyclopentane Azeotrope-Like Compositions:

In a preferred embodiment, the azeotrope-like composition comprises effective amounts of cis-HFO-1233zd and cyclopentane. More preferably, these binary azeotrope-like compositions consist essentially of about 42 to about 99 wt. % cis-HFO-1233zd and from about 1 to about 58 wt. % cyclopentane, more preferably from about 50 to about 95 wt. % cis-HFO-1233zd and about 5 to about 50 wt. % cyclopentane, and even more preferably from about 60 to about 93 wt. % cis-HFO-1233zd and from about 7 to about 40 wt. % cyclopentane. Preferably, the cis-HFO-1233zd/cyclopentane compositions of the present invention have a normal boiling point of about 34.7° C.±1° C. at ambient pressure.

Trans-HFO-1233zd/Cyclopentene Azeotrope-Like Compositions:

In a preferred embodiment, the azeotrope-like composition comprises effective amounts of trans-HFO-1233zd and cyclopentene. More preferably, these binary azeotrope-like compositions consist essentially of about 95 to about 99.9 wt. % trans-HFO-1233zd and from about 0.1 to about 5 wt. % cyclopentene, more preferably from about 97 to about 99.9 wt. % trans-HFO-1233zd and about 0.1 to about 3 wt. % cyclopentene, and even more preferably from about 98 to about 99.9 wt. % trans-HFO-1233zd and from about 2 to about 98 wt. % cyclopentene.

Preferably, the trans-HFO-1233zd/cyclopentene compositions of the present invention have a normal boiling point of about 18.1° C.±1° C. at ambient pressure.

Trans-HFO-1233zd/n-Hexane Azeotrope-Like Compositions:

In a preferred embodiment, the azeotrope-like composition comprises effective amounts of trans-HFO-1233zd and n-hexane. More preferably, these binary azeotrope-like compositions consist essentially of about 95 to about 99.99 wt. % trans-HFO-1233zd and from about 0.01 to about 5 wt. % n-hexane, more preferably from about 97 to about 99.99 wt. % trans-HFO-1233zd and about 0.01 to about 3 wt. % n-hexane, and even more preferably from about 97.2 to about 99.99 wt. % trans-HFO-1233zd and from about 0.01 to about 2.8 wt. % n-hexane.

Preferably, the trans-HFO-1233zd/n-hexane compositions of the present invention have a normal boiling point of about 17.4° C.±1° C. at ambient pressure.

Cis-HFO-1233zd/n-Hexane Azeotrope-Like Compositions:

In a preferred embodiment, the azeotrope-like composition comprises effective amounts of cis-HFO-1233zd and n-hexane. More preferably, these binary azeotrope-like compositions consist essentially of about 80 to about 99.5 wt. % cis-HFO-1233zd and from about 0.5 to about 20 wt. % n-hexane, more preferably from about 90 to about 99.5 wt. % cis-HFO-1233zd and about 0.5 to about 10 wt. % n-hexane, and even more preferably from about 95 to about 99.5 wt. % cis-HFO-1233zd and from about 0.5 to about 5 wt. % n-hexane.

Preferably, the cis-HFO-1233zd/n-hexane compositions of the present invention have a normal boiling point of about 39° C.±1° C. at ambient pressure.

Trans-HFO-1233zd/Isohexane Azeotrope-Like Compositions:

In a preferred embodiment, the azeotrope-like composition comprises effective amounts of trans-HFO-1233zd and isohexane. More preferably, these binary azeotrope-like compositions consist essentially of about 94.4 to about 99.99 wt. % trans-HFO-1233zd and from about 0.01 to about 5.6 wt. % isohexane, more preferably from 96 wt. % to about 99.99 wt. % trans-HFO-1233zd and about 0.01 to about 4 wt. % isohexane, and even more preferably from about 97 to about 99.99 wt. % trans-HFO-1233zd and from about 0.01 to about 3 wt. % isohexane.

Preferably, the trans-HFO-1233zd/isohexane compositions of the present invention have a boiling point of from about 17° C. to about 19° C., more preferably about 17° C. to about 18° C., even more preferably about 17.3° C. to about 17.6° C., and most preferably about 17.4° C.±1° C., all measured at ambient pressure.

Cis-HFO-1233zd/Isohexane Azeotrope-Like Compositions:

In a preferred embodiment, the azeotrope-like composition comprises effective amounts of cis-HFO-1233zd and isohexane. More preferably, these binary azeotrope-like compositions consist essentially of about 70 to about 99.5 wt. % cis-HFO-1233zd and from about 0.5 to about 30 wt. % isohexane, more preferably from 85 wt. % to about 99.5 wt. % cis-HFO-1233zd and about 0.5 to about 15 wt. % isohexane, and even more preferably from about 93 to about 99.5 wt. % cis-HFO-1233zd and from about 0.5 to about 7 wt. % isohexane.

Preferably, the cis-HFO-1233zd/isohexane compositions of the present invention have a normal boiling point of about 37° C.±1° C.

In a preferred embodiments, the azeotrope-like composition comprises effective amounts of HFO-1233zd and a hydrohalocarbon. Preferably, the hydrohalocarbon is selected from the group consisting of 1-chloropropane, 2-chloropropane, 1,1,1,3,3-pentafluorobutane (HFC-365mfc), and trans-1,2-dichloroethylene (trans-1,2-DCE). In certain preferred embodiments, the HFO-1233zd is trans-HFO-1233zd. In certain other embodiments, the HFO-1233zd is cis-HFO-1233zd.

Trans-HFO-1233zd/1-Chloropropane Azeotrope-Like Compositions:

In a preferred embodiment, the azeotrope-like composition comprises effective amounts of trans-HFO-1233zd and 1-chloropropane. More preferably, these binary azeotrope-like compositions consist essentially of about 96 to about 99.9 wt. % trans-HFO-1233zd and from about 0.1 to about 4 wt. % 1-chloropropane, more preferably from about 98 to about 99.9 wt. % trans-HFO-1233zd and about 0.1 to about 2 wt. % 1-chloropropane, and even more preferably from about 99 to about 99.9 wt. % trans-HFO-1233zd and from about 0.1 to about 1 wt. % 1-chloropropane.

Preferably, the trans-HFO-1233zd/1-chloropropane compositions of the present invention have a normal boiling point of about 18° C.±1° C. at ambient pressure.

Trans-HFO-1233zd/2-Chloropropane Azeotrope-Like Compositions:

In a preferred embodiment, the azeotrope-like composition comprises effective amounts of trans-HFO-1233zd and 2-chloropropane. More preferably, these binary azeotrope-like compositions consist essentially of about 94 to about 99.9 wt. % trans-HFO-1233zd and from about 0.1 to about 6 wt. % 2-chloropropane, more preferably from about 97 to about 99.9 wt. % trans-HFO-1233zd and about 0.1 to about 3 wt. % 2-chloropropane, and even more preferably from about 99 to about 99.9 wt. % trans-HFO-1233zd and from about 0.1 to about 1 wt. % 2-chloropropane.

Preferably, the trans-HFO-1233zd/2-chloropropane compositions of the present invention have a normal boiling point of about 17.8° C.±1° C. at ambient pressure.

Trans-HFO-1233zd/HFC-365mfc Azeotrope-Like Compositions:

In a preferred embodiment, the azeotrope-like composition comprises effective amounts of trans-HFO-1233zd and HFC-365mfc. More preferably, these binary azeotrope-like compositions consist essentially of about 89 to about 99.9 wt. % trans-HFO-1233zd and from about 0.1 to about 11 wt. % HFC-365mfc, more preferably from about 92.5 to about 99.9 wt. % trans-HFO-1233zd and about 0.1 to about 7.5 wt. % HFC-365mfc, and even more preferably from about 95 to about 99.9 wt. % trans-HFO-1233zd and from about 0.1 to about 5 wt. % HFC-365mfc.

Trans-HFO-1233zd/trans-1,2-DCE Azeotrope-Like Compositions:

In a preferred embodiment, the azeotrope-like composition comprises effective amounts of trans-HFO-1233zd and trans-1,2-DCE. More preferably, these binary azeotrope-like compositions consist essentially of about 60 to about 99.99 wt. % trans-HFO-1233zd and from about 0.01 to about 40 wt. % trans-1,2-DCE, more preferably from about 75 to about 99.99 wt. % trans-HFO-1233zd and about 0.01 to about 25 wt. % trans-1,2-DCE, and even more preferably from about 95 weight percent to about 99.99 wt % trans-HFO-1233zd and from about 0.01 to about 5 wt. % trans-1,2-DCE.

Preferably, the trans-HFO-1233zd/trans-1,2-DCE compositions of the present invention have a boiling of from about 17° C. to about 19° C., more preferably about 17.5° C. to about 18.5° C., even more preferably about 17.5° C. to about 18° C., and most preferably about 17.8° C.±1° C., all measured at ambient pressure.

Cis-HFO-1233zd/trans-1,2-DCE Azeotrope-Like Compositions:

In a preferred embodiment, the azeotrope-like composition comprises effective amounts of cis-HFO-1233zd and trans-1,2-DCE. More preferably, these binary azeotrope-like compositions consist essentially of about 42 to about 99.9 wt. % cis-HFO-1233zd and from about 0.1 to about 58 wt. % trans-1,2-DCE, more preferably from about 55 to about 99.5 wt. % cis-HFO-1233zd and about 0.5 to about 45 wt. % trans-1,2-DCE, and even more preferably from about 65 weight percent to about 99 wt % cis-HFO-1233zd and from about 1 to about 35 wt. % trans-1,2-DCE.

Preferably, the cis-HFO-1233zd/trans-1,2-DCE compositions of the present invention have a boiling point of about 37.0° C.±1° C. at ambient pressure.

Trans-HFO-1233zd/methylal Azeotrope-Like Compositions:

In a preferred embodiment, the azeotrope-like composition comprises effective amounts of trans-HFO-1233zd and methylal. More preferably, these binary azeotrope-like compositions consist essentially of about 95 to about 99.9 wt. % trans-HFO-1233zd and from about 0.1 to about 5 wt. % methylal, more preferably from about 97 to about 99.9 wt. % trans-HFO-1233zd and about 0.1 to about 3 wt. % methylal, and even more preferably from about 98.5 weight percent to about 99.9 wt % trans-HFO-1233zd and from about 0.1 to about 1.5 wt. % methylal.

Preferably, the trans-HFO-1233zd/methylal compositions of the present invention have a normal boiling point of about 17.3° C.±1° C. at ambient pressure.

Trans-HFO-1233zd/methyl acetate Azeotrope-Like Compositions:

In a preferred embodiment, the azeotrope-like composition comprises effective amounts of trans-HFO-1233zd and methyl acetate. More preferably, these binary azeotrope-like compositions consist essentially of about 90 to about 99.9 wt. % trans-HFO-1233zd and from about 0.1 to about 10 wt. % methyl acetate, more preferably from about 95 to about 99.9 wt. % trans-HFO-1233zd and about 0.1 to about 5 wt. % methyl acetate, and even more preferably from about 98.5 weight percent to about 99.9 wt % trans-HFO-1233zd and from about 0.1 to about 1.5 wt. % methyl acetate.

Preferably, the trans-HFO-1233zd/methyl acetate compositions of the present invention have a normal boiling point of about 17.5° C.±1° C. at ambient pressure.

Trans-HFO-1233zd/water Azeotrope-Like Compositions:

In a preferred embodiment, the azeotrope-like composition comprises effective amounts of trans-HFO-1233zd and water. More preferably, these binary azeotrope-like compositions consist essentially of about 70 to about 99.95 wt. % trans-HFO-1233zd and from about 0.05 to about 30 wt. % water, more preferably from about 86 to about 99.95 wt. % trans-HFO-1233zd and about 0.05 to about 14 wt. % water, and most preferably about 90 to about 99.95 wt. % trans-HFO-1233zd and about 0.05 to about 10 wt. % water.

Preferably, the trans-HFO-1233zd/water compositions of the present invention have a boiling point of about 17.4° C.±1° C. at ambient pressure.

Trans-HFO-1233zd/Nitromethane Azeotrope-Like Compositions:

In a preferred embodiment, the azeotrope-like composition comprises effective amounts of trans-HFO-1233zd and nitromethane. More preferably, these binary azeotrope-like compositions consist essentially of about 98 to about 99.99 wt. % trans-HFO-1233zd and from about 0.01 to about 2 wt. % nitromethane, more preferably from about 99 to about 99.99 wt. % trans-HFO-1233zd and about 0.01 to about 1 wt. % nitromethane, and even more preferably from about 99.9 to about 99.99 wt. % trans-HFO-1233zd and from about 0.01 to about 0.1 wt. % nitromethane.

Preferably, the trans-HFO-1233zd/nitromethane compositions of the present invention have a normal boiling point of about 17.4° C.±1° C. at ambient pressure.

Cis-HFO-1233zd/Nitromethane Azeotrope-Like Compositions:

In a preferred embodiment, the azeotrope-like composition comprises effective amounts of cis-HFO-1233zd and nitromethane. More preferably, these binary azeotrope-like compositions consist essentially of about 95 to about 99.9 wt. % cis-HFO-1233zd and from about 0.1 to about 5 wt. % nitromethane, more preferably from about 97 to about 99.9 wt. % cis-HFO-1233zd and about 0.1 to about 3 wt. % nitromethane, and even more preferably from about 99 to about 99.9 wt. % cis-HFO-1233zd and from about 0.1 to about 1 wt. % nitromethane.

Preferably, the cis-HFO-1233zd/nitromethane compositions of the present invention have a normal boiling point of about 39° C.±1° C. at ambient pressure.

Trans-HFO-1233zd/trans-1,2-DCE/Methanol Azeotrope-Like Compositions:

In a preferred embodiment, the azeotrope-like composition comprises effective amounts of trans-HFO-1233zd, methanol, and trans-1,2-DCE. More preferably, these ternary azeotrope-like compositions consist essentially of about 80 to about 99.9 wt. % trans-HFO-1233zd, from about 0.05 to about 15 wt. % methanol, and from about 0.05 to about 10 wt. % trans-1,2-DCE, even more preferably from about 90 to about 99.9 wt. % trans-HFO-1233zd, from about 0.05 to about 9 wt. % methanol, and about 0.05 to about 5 wt. % trans-1,2-DCE, and most preferably from about 95 to about 99.9 wt. % trans-HFO-1233zd, from about 0.05 to about 5 wt. % methanol, and from about 0.05 to about 3 wt. % trans-1,2-DCE.

Preferably, the trans-HFO-1233zd/methanol/trans-1,2-DCE compositions of the present invention have a boiling point of from about 16.6° C.±1° C. at ambient pressure Trans-HFO-1233zd/Methanol/n-Pentane Azeotrope-Like Compositions:

In a preferred embodiment, the azeotrope-like composition comprises effective amounts of trans-HFO-1233zd, methanol, and n-pentane. More preferably, these ternary azeotrope-like compositions consist essentially of about 55 to about 99.90 wt. % trans-HFO-1233zd, from about 0.05 to about 10 wt. % methanol, and from about 0.05 to about 35 wt. % n-pentane, even more preferably from about 79 to about 98 wt. % trans-HFO-1233zd, from about 0.1 to about 5 wt. % methanol, and about 1.9 to about 16 wt. % n-pentane, and most preferably from about 88 to about 96 wt. % trans-HFO-1233zd, from about 0.5 to about 4 wt. % methanol, and from about 3.5 to about 8 wt. % n-pentane.

Preferably, the trans-HFO-1233zd/methanol/n-pentane compositions of the present invention have a boiling point of from about 17° C. to about 19° C., more preferably about 17° C. to about 18° C., even more preferably about 17.1° C. to about 17.6° C., and most preferably about 17.4° C.±1° C., all measured at a pressure of about 14 psia.

The azeotrope-like compositions of the present invention may further include a variety of optional additives including, but not limited to, lubricants, stabilizers, metal passivators, corrosion inhibitors, flammability suppressants, and the like. Examples of suitable stabilizers include diene-based compounds, and/or phenol compounds, and/or epoxides selected from the group consisting of aromatic epoxides, alkyl epoxides, alkenyl epoxides, and combinations of two or more thereof. Preferably, these optional additives do not affect the basic azeotrope-like characteristic of the composition.

Blowing Agents:

In another embodiment of the invention, provided are blowing agents comprising at least one azeotrope-like mixture described herein. Polymer foams are generally of two general classes: thermoplastic foams and thermoset foams.

Thermoplastic foams are produced generally via any method known in the art, including those described in Throne, *Thermoplastic Foams*, 1996, Sherwood Publishers, Hinkley, Ohio, or Klempner and Sendijarevic, *Polymeric Foams and Foam Technology*, 2$^{nd}$ Edition 2004, Hander Gardner Publications. Inc, Cincinnati, Ohio. For example, extruded thermoplastic foams can be prepared by an extrusion process whereby a solution of blowing agent in molten polymer, formed in an extruder under pressure, is forced through an orifice onto a moving belt at ambient temperature or pressure or optionally at reduced pressure to aid in foam expansion. The blowing agent vaporizes and causes the polymer to expand. The polymer simultaneously expands and cools under conditions that give it enough strength to maintain dimensional stability at the time corresponding to maximum expansion. Polymers used for the production of extruded thermoplastic foams include, but are not limited to, polystyrene, polyethylene (HDPE, LDPE, and LLDPE), polypropylene, polyethylene terephthalate, ethylene vinyl acetate, and mixtures thereof. A number of additives are optionally added to the molten polymer solution to optimize foam processing and properties including, but not limited to, nucleating agents (e.g., talc), flame retardants, colorants, processing aids (e.g., waxes), cross linking agents, permeability modifiers, and the like. Additional processing steps such as irradiation to increase cross linking, lamination of a surface film to improve foam skin quality, trimming and planning to achieve foam dimension requirements, and other processes may also be included in the manufacturing process.

In general, the blowing agent may include the azeotrope-like compositions of the present invention in widely ranging amounts. It is generally preferred, however, that the blowing agents comprise at least about 15% by weight of the blowing agent. In certain preferred embodiments, the blowing agent comprises at least about 50% by weight of the present compositions, and in certain embodiments the blowing agent consists essentially of the present azeotrope-like composition. In certain preferred embodiments, the blowing agent includes, in addition to the present azeotrope-like mixtures, one or more co-blowing agents, fillers, vapor pressure modifiers, flame suppressants, stabilizers, and like adjuvants.

In certain preferred embodiments, the blowing agent is characterized as a physical (i.e., volatile) blowing agent comprising the azeotrope-like mixture of the present invention. In general, the amount of blowing agent present in the blended mixture is dictated by the desired foam densities of the final foams products and by the pressure and solubility limits of the process. For example, the proportions of blowing agent in parts by weight can fall within the range of about 1 to about 45 parts, more preferably from about 4 to about 30 parts, of blowing agent per 100 parts by weight of polymer. The blowing agent may comprise additional components mixed with the azeotrope-like composition, including chlorofluorocarbons such as trichlorofluoromethane (CFC-11), dichlorodifluoromethane (CFC-12), hydrochlorofluorocarbons such as 1,1-dichloro-1-fluoroethane (HCFC-141b), 1-chloro-1,1-difluoroethane (HCFC-142b), chlorodifluoromethane (HCFC-22), hydrofluorocarbons such as 1,1,1,2-tetrafluoroethane (HFC-134a), 1,1-difluoroethane (HFC-152a), 1,1,1,3,3-pentafluoropropane (HFC-245fa), and 1,1,1,3,3-pentafluorobutane (HFC-365mfc), hydrocarbons such as propane, butane, isobutane, cyclopentane, carbon dioxide, chlorinated hydrocarbons alcohols, ethers, ketones and mixtures thereof.

In certain embodiments, the blowing agent is characterized as a chemical blowing agent. Chemical blowing agents are materials that, when exposed to temperature and pressure conditions in the extruder, decompose to liberate a gas, generally carbon dioxide, carbon monoxide, nitrogen, hydrogen, ammonia, nitrous oxide, of mixtures thereof. The amount of chemical blowing agent present is dependent on the desired final foam density. The proportions in parts by weight of the total chemical blowing agent blend can fall within the range of from less than 1 to about 15 parts, preferably from about 1 to about 10 parts, of blowing agent per 100 parts by weight of polymer.

In certain preferred embodiments, dispersing agents, cell stabilizers, surfactants and other additives may also be incorporated into the blowing agent compositions of the present invention. Surfactants are optional, but preferably are added to serve as cell stabilizers. Some representative materials are sold under the names of DC-193, B-8404, and L-5340 which are, generally, polysiloxane polyoxyalkylene block co-polymers such as those disclosed in U.S. Pat. Nos. 2,834,748, 2,917,480, and 2,846,458, each of which are incorporated herein by reference. Other optional additives for the blowing agent mixture include flame retardants or suppressants such as tri(2-chloroethyl)phosphate, tri(2-chloropropyl)phosphate, tri(2,3-dibromopropyl)-phosphate, tri(1,3-dichloropropyl)phosphate, diammonium phosphate, various halogenated aromatic compounds, antimony oxide, aluminum trihydrate, polyvinyl chloride, and the like. With respect to thermoset foams, in general any thermoset polymer can be used, including but not limited to polyurethane, polyisocyanurate, phenolic, epoxy, and combinations thereof. In general these foams are produced by bringing together chemically reactive components in the presence of one or more blowing agents, including the azeotrope-like composition of this invention and optionally other additives, including but not limited to cell stabilizers, solubility enhancers, catalysts, flame retardants, auxiliary blowing agents, inert fillers, dyes, and the like. With respect to the preparation of polyurethane or polyisocyanurate foams using the azeotrope like compositions described in the invention, any of the methods well known in the art can be employed, see Saunders and Frisch, *Volumes I and II Polyurethanes Chemistry and Technology* (1962) John Wiley and Sons, New York, N.Y. In general, polyurethane or polyisocyanurate foams are prepared by combining an isocyanate, a polyol or mixture of polyols, a blowing agent or mixture of blowing agents, and other materials such as catalysts, surfactants, and optionally, flame retardants, colorants, or other additives.

It is convenient in many applications to provide the components for polyurethane or polyisocyanurate foams in preblended formulations. Most typically, the foam formulation is preblended into two components. The isocyanate and optionally certain surfactants and blowing agents comprise the first component, commonly referred to as the "A" component. The polyol or polyol mixture, surfactant, catalysts, blowing agents, flame retardant, and other isocyanate reactive components comprise the second component, commonly referred to as the "B" component. Accordingly, polyurethane or polyisocyanurate foams are readily prepared by bringing together the A and B side components either by hand mix for small preparations and, preferably, machine mix techniques to form blocks, slabs, laminates, pour-in-place panels and other items, spray applied foams, froths, and the like. Optionally, other ingredients such as fire retardants, colorants, auxiliary blowing agents, water, and even other polyols can be added as a third stream to the mix head or reaction site. Most conveniently, however, they are all incorporated into one B Component as described above.

Any organic polyisocyanate can be employed in polyurethane or polyisocyanurate foam synthesis inclusive of aliphatic and aromatic polyisocyanates. Preferred as a class are the aromatic polyisocyanates. Typical aliphatic polyisocyanates are alkylene diisocyanates such as tri, tetra, and hexamethylene diisocyanate, isophorene diisocyanate, 4,4'-methylenebis(cyclohexyl isocyanate), and the like; typical aromatic polyisocyanates include m-, and p-phenylene diisocyanate, polymethylene polyphenyl isocyanate, 2,4- and 2,6-toluenediisocyanate, dianisidine diisocyanate, bitoylene isocyanate, naphthylene 1,4-diisocyanate, bis(4-isocyanatophenyl)methene, bis(2-methyl-4-isocyanatophenyl)methane, and the like.

Preferred polyisocyanates are the polymethylene polyphenyl isocyanates, particularly the mixtures containing from about 30 to about 85 percent by weight of methylenebis (phenyl isocyanate) with the remainder of the mixture comprising the polymethylene polyphenyl polyisocyanates of functionality higher than 2.

Typical polyols used in the manufacture of polyurethane foams include, but are not limited to, aromatic amino-based polyether polyols such as those based on mixtures of 2,4- and 2,6-toluenediamine condensed with ethylene oxide and/or propylene oxide. These polyols find utility in pour-in-place molded foams. Another example is aromatic alkylamino-based polyether polyols such as those based on ethoxylated and/or propoxylated aminoethylated nonylphenol derivatives. These polyols generally find utility in spray applied polyurethane foams. Another example is sucrose-based polyols such as those based on sucrose derivatives and/or mixtures of sucrose and glycerine derivatives condensed with ethylene oxide and/or propylene oxide.

Examples of polyols used in polyurethane modified polyisocyanurate foams include, but are not limited to, aromatic polyester polyols such as those based on complex mixtures of phthalate-type or terephthalate-type esters formed from polyols such as ethylene glycol, diethylene glycol, or propylene glycol. These polyols are used in rigid laminated boardstock, can be blended with other types of polyols such as sucrose based polyols, and used in other polyurethane foam applications such as described above.

Catalysts used in the manufacture of polyurethane foams are typically tertiary amines including, but not limited to, N-alkylmorpholines, N-alkylalkanolamines, N,N-dialkylcyclohexylamines, and alkylamines where the alkyl groups are methyl, ethyl, propyl, butyl, and the like and isomeric forms thereof; and hetrocyclic amines. Typical, but not limiting examples are triethylenediamine, tetramethylethylenediamine, bis(2-dimethylaminoethyl)ether, triethylamine, tripropylamine, tributylamine, triamylamine, pyridine, quinoline, dimethylpiperazine, piperazine, N,N-dimethylcyclohexylamine, N-ethylmorpholine, 2-methylpiperazine, N,N-dimethylethanolamine, tetramethylpropanediamine, methyltriethylenediamine, and the like, and mixtures thereof.

Optionally, non-amine polyurethane catalysts are used. Typical of such catalysts are organometallic compounds of bismuth, lead, tin, titanium, antimony, uranium, cadmium, cobalt, thorium, aluminum, mercury, zinc, nickel, cerium, molybdenum, vanadium, copper, manganese, zirconium, and the like. Included as illustrative are bismuth nitrate, lead 2-ethylhexoate, lead benzoate, ferric chloride, antimony trichloride and antimony glycolate. A preferred organo-tin class includes the stannous salts of carboxylic acids such as stannous octoate, stannous 2-ethylhexoate, stannous laurate, and the like, as well as dialkyl tin salts of carboxylic acids such as dibutyl tin diacetate, dibutyl tin dilaurate, dioctyl tin diacetate, and the like.

In the preparation of polyisocyanurate foams, trimerization catalysts are used for the purpose of converting the blends in conjunction with excess A component to polyisocyanurate-polyurethane foams. The trimerization catalysts employed can be any catalyst known to one skilled in the art, including, but not limited to, glycine salts and tertiary amine trimerization catalysts and alkali metal carboxylic acid salts and mixtures of the various types of catalysts. Preferred species within the classes are potassium acetate, potassium octoate, and N-(2-hydroxy-5-nonylphenol)methyl-N-methylglycinate.

Dispersing agents, cell stabilizers, and surfactants can be incorporated into the present blends. Surfactants, which are, generally, polysiloxane polyoxyalkylene block co-polymers, such as those disclosed in U.S. Pat. Nos. 2,834,748, 2,917,480, and 2,846,458, which are incorporated herein by reference.

Other optional additives for the blends can include flame retardants such as tris(2-chloroethyl)phosphate, tris(2-chloropropyl)phosphate, tris(2,3-dibromopropyl)phosphate, tris (1,3-dichloropropyl)phosphate, diammonium phosphate, various halogenated aromatic compounds, antimony oxide, aluminum trihydrate, polyvinyl chloride, and the like. Other optional ingredients can include from 0 to about 3 percent water, which chemically reacts with the isocyanate to produce carbon dioxide. This carbon dioxide acts as an auxiliary blowing agent.

Also included in the mixture are blowing agents or blowing agent blends as disclosed in this invention. Generally speaking, the amount of blowing agent present in the blended mixture is dictated by the desired foam densities of the final polyurethane or polyisocyanurate foams product. The proportions in parts by weight of the total blowing agent blend can fall within the range of from 1 to about 45 parts of blowing agent per 100 parts of polyol, preferably from about 4 to about 30 parts.

The polyurethane foams produced can vary in density from about 0.5 pound per cubic foot to about 40 pounds per cubic foot, preferably from about 1.0 to 20.0 pounds per cubic foot, and most preferably from about 1.5 to 6.0 pounds per cubic foot. The density obtained is a function of how much of the blowing agent or blowing agent mixture disclosed in this invention is present in the A and/or B components, or alternatively added at the time the foam is prepared.

Foams and Foamable Compositions:

Certain embodiments of the present invention involve a foam comprising a polyurethane-, polyisocyanurate-, or phenolic-based cell wall and a cell gas disposed within at least a portion of the cells, wherein the cell gas comprises the azeotrope-like mixture described herein. In certain embodiments, the foams are extruded thermoplastic foams. Preferred foams have a density ranging from about 0.5 pounds per cubic foot to about 60 pounds per cubic foot, preferably from about 1.0 to 20.0 pounds per cubic foot, and most preferably from about 1.5 to 6.0 pounds per cubic foot. The foam density is a function of how much of the blowing agent or blowing agent mixture (i.e., the azeotrope-like mixture and any auxiliary blowing agent, such as carbon dioxide, chemical blowing agent or other co-blowing agent) is present in the molten polymer. These foams are generally rigid but can be made in various grades of softness to suit the end use requirements. The foams can have a closed cell structure, an open cell structure or a mixture of open and closed cells, with closed cell structures being preferred. These foams are used in a variety of well known applications, including but not limited to thermal insulation, flotation, packaging, void filling, crafts and decorative, and shock absorption.

In other embodiments, the invention provides foamable compositions. The foamable compositions of the present invention generally include one or more components capable of forming foam, such as polyurethane, polyisocyanurate, and phenolic-based compositions, and a blowing agent comprising at least one azeotrope-like mixture described herein. In certain embodiments, the foamable composition comprises thermoplastic materials, particularly thermoplastic polymers and/or resins. Examples of thermoplastic foam components include polyolefins, such as polystyrene (PS), polyethylene (PE), polypropylene (PP) and polyethylene-terepthalate (PET), and foams formed therefrom, preferably low-density foams. In certain embodiments, the thermoplastic foamable composition is an extrudable composition.

In certain embodiments, provided is a method for producing such foams. It will be appreciated by those skilled in the art, especially in view of the disclosure contained herein, that the order and manner in which the blowing agent is formed and/or added to the foamable composition does not generally affect the operability of the present invention. For example, in the case of extrudable foams, it is possible to mix in advance the various components of the blowing agent. In certain embodiments, the components of the foamable composition are not mixed in advance of introduction to the extrusion equipment or are not added to the same location in the extrusion equipment. Thus, in certain embodiments it may be desired to introduce one or more components of the blowing agent at first location in the extruder, which is upstream of the place of addition of one or more other components of the blowing agent, with the expectation that the components will come together in the extruder and/or operate more effectively in this manner. In certain other embodiments, two or more components of the blowing agent are combined in advance and introduced together into the foamable composition, either directly or as part of premix which is then further added to other parts of the foamable composition.

Sprayable Compositions:

In a preferred embodiment, the azeotrope-like compositions of this invention may be used as solvents in sprayable compositions, either alone or in combination with other known propellants. The solvent composition comprises, more preferably consists essentially of, and, even more preferably, consists of the azeotrope-like compositions of the invention. In certain embodiments, the sprayable composition is an aerosol.

In certain preferred embodiments, provided is a sprayable composition comprising a solvent as described above, an active ingredient, and optionally, other components such as inert ingredients, solvents, and the like.

Suitable active materials to be sprayed include, without limitation, cosmetic materials such as deodorants, perfumes, hair sprays, cleaning solvents, lubricants, insecticides as well as medicinal materials, such as anti-asthma medications. The term medicinal materials is used herein in its broadest sense to include any and all materials which are, or at least are believe to be, effective in connection with therapeutic, diagnostic, pain relief, and similar treatments, and as such would include for example drugs and biologically active substances.

Solvents and Cleaning Compositions:

In another embodiment of the invention, the azeotrope-like compositions described herein can be used as a solvent in cleaning various soils such as mineral oil, rosin based fluxes, silicon oils, lubricants, etc., from various substrates by wiping, vapor degreasing, or other means. In certain preferred embodiments, the cleaning composition is an aerosol.

EXAMPLES

The invention is further illustrated in the following example which is intended to be illustrative, but not limiting in any manner. For the relevant examples, an ebulliometer of the general type described by Swietolslowski in his book "Ebulliometric Measurements" (Reinhold, 1945) was used.

Example 1

An ebulliometer consisting of vacuum jacketed tube with a condenser on top which was further equipped with a Quartz Thermometer or a thermistor was used. About 10 cc of trans-HFO-1233zd was charged to the ebulliometer and then methanol was added in small, measured increments. Temperature depression was observed when methanol was added, indicating a binary minimum boiling azeotrope had been formed. From greater than 0 to about 51 weight percent methanol, the boiling point of the composition changes less than about 1.3° C. The boiling points of the binary mixtures shown in Table 1 changed by less than about 0.02° C. Thus the compositions exhibited azeotrope and/or azeotrope-like properties over these ranges. To conform result two such ebulliometers were set up side by side of which one contained pure solvent and the other one was set up with trans-HFO-1233zd and $2^{nd}$ component was added as mentioned before. The difference of temperatures in the two was also measured.

TABLE 1 trans-HFO-1233zd/Methanol compositions at ambient pressure

| Temp (° C.) | Wt. % trans-HFO-1233zd | wt % Methanol |
| --- | --- | --- |
| 17.15 (° C.) | 98.78 wt. % | 1.22 wt. % |
| 17.14 (° C.) | 98.58 wt. % | 1.42 wt. % |
| 17.14 (° C.) | 98.38 wt. % | 1.62 wt. % |
| 17.14 (° C.) | 98.18 wt. % | 1.82 wt. % |
| 17.14 (° C.) | 97.98 wt. % | 2.02 wt. % |
| 17.14 (° C.) | 97.78 wt. % | 2.22 wt. % |
| 17.15 (° C.) | 97.59 wt. % | 2.41 wt. % |

Example 2

An ebulliometer consisting of vacuum jacketed tube with a condenser on top which was further equipped with a Quartz Thermometer or a thermistor was used. About 35 g trans-HFO-1233zd is charged to the ebulliometer and then n-pentane was added in small, measured increments. Temperature depression was observed when n-pentane was added to trans-HFO-1233zd, indicating a binary minimum boiling azeotrope had been formed. From greater than 0 to about 30 weight percent n-pentane, the boiling point of the composition changes less than about 0.8° C. The boiling points of the binary mixtures shown in Table 2 changed by less than about 0.02° C. Thus the compositions exhibited azeotrope and/or azeotrope-like properties over these ranges.

TABLE 2 trans-HFO-1233zd/n-Pentane compositions at ambient pressure

| Temp (° C.) | Wt. % trans-HFO-1233zd | Wt % n-pentane |
| --- | --- | --- |
| 17.43 (° C.) | 97.76 wt. % | 2.24 wt. % |
| 17.42 (° C.) | 97.60 wt. % | 2.40 wt. % |
| 17.42 (° C.) | 97.45 wt. % | 2.55 wt. % |
| 17.42 (° C.) | 97.29 wt. % | 2.71 wt. % |
| 17.42 (° C.) | 97.14 wt. % | 2.86 wt. % |
| 17.42 (° C.) | 96.98 wt. % | 3.02 wt. % |
| 17.42 (° C.) | 96.83 wt. % | 3.17 wt. % |
| 17.42 (° C.) | 96.67 wt. % | 3.33 wt. % |
| 17.42 (° C.) | 96.52 wt. % | 3.48 wt. % |
| 17.42 (° C.) | 96.37 wt. % | 3.63 wt. % |
| 17.42 (° C.) | 96.22 wt. % | 3.78 wt. % |
| 17.42 (° C.) | 96.07 wt. % | 3.93 wt. % |
| 17.43 (° C.) | 95.92 wt. % | 4.08 wt. % |

Example 3

An ebulliometer consisting of vacuum jacketed tube with a condenser on top which was further equipped with a Quartz Thermometer or a thermistor was used. About 17 g trans-HFO-1233zd is charged to the ebulliometer and then isopentane was added in small, measured increments. Temperature depression was observed when isopentane was added to trans-HFO-1233zd, indicating a binary minimum boiling azeotrope had been formed. From greater than about 0 to about 30 weight percent isopentane, the boiling point of the composition changed by about 0.8° C. or less. The boiling points of the binary mixtures shown in Table 3 changed by less than about 0.2° C. Thus the compositions exhibited azeotrope and/or azeotrope-like properties over these ranges.

TABLE 3 trans-HFO-1233/isopentane compositions at ambient pressure

| Temp(° C.) | Wt % trans-HFO-1233zd | Wt % isopentane |
| --- | --- | --- |
| 16.86 (° C.) | 92.39 wt. % | 7.61 wt. % |
| 16.78 (° C.) | 90.52 wt. % | 9.48 wt. % |
| 16.73 (° C.) | 88.73 wt. % | 11.27 wt. % |
| 16.70 (° C.) | 87.01 wt. % | 12.99 wt. % |
| 16.70 (° C.) | 85.35 wt. % | 14.65 wt. % |
| 16.69 (° C.) | 83.75 wt. % | 16.25 wt. % |
| 16.70 (° C.) | 82.21 wt. % | 17.79 wt. % |
| 16.72 (° C.) | 80.73 wt. % | 19.27 wt. % |
| 16.76 (° C.) | 79.13 wt. % | 20.87 wt. % |
| 16.85 (° C.) | 77.58 wt. % | 22.42 wt. % |

Example 4

An ebulliometer consisting of vacuum jacketed tube with a condenser on top which was further equipped with a Quartz Thermometer or a thermistor was used. About 17 g neopentane is charged to the ebulliometer and then trans-HFO-1233zd was added in small, measured increments. Temperature depression was observed when trans-HFO-1233zd was added to neopentane indicating a binary minimum boiling azeotrope had been formed. As shown in Table 4, compositions comprising from about 19 to about 49 weight percent trans-HFO-1233zd had a change in boiling point of 0.1° C. or less. Thus the compositions exhibited azeotrope and/or azeotrope-like properties over at least this range.

TABLE 4 trans-HFO-1233zd/neopentane compositions at ambient pressure

| Temp(° C.) | Wt % trans-HFO-1233zd | Wt % neopentane |
|---|---|---|
| 8.54 (° C.) | 0.00 wt. % | 100.00 wt. % |
| 8.47 (° C.) | 1.36 wt. % | 98.64 wt. % |
| 8.42 (° C.) | 2.69 wt. % | 97.31 wt. % |
| 8.30 (° C.) | 5.23 wt. % | 94.77 wt. % |
| 8.21 (° C.) | 7.65 wt. % | 92.35 wt. % |
| 8.12 (° C.) | 9.94 wt. % | 90.06 wt. % |
| 7.95 (° C.) | 14.21 wt. % | 85.79 wt. % |
| 7.87 (° C.) | 19.00 wt. % | 81.00 wt. % |
| 7.78 (° C.) | 23.29 wt. % | 76.71 wt. % |
| 7.72 (° C.) | 29.28 wt. % | 70.72 wt. % |
| 7.72 (° C.) | 34.40 wt. % | 65.60 wt. % |
| 7.75 (° C.) | 38.83 wt. % | 61.17 wt. % |
| 7.81 (° C.) | 42.70 wt. % | 57.30 wt. % |
| 7.85 (° C.) | 46.11 wt. % | 53.89 wt. % |
| 7.88 (° C.) | 49.14 wt. % | 50.86 wt. % |

Example 5

An ebulliometer consisting of vacuum jacketed tube with a condenser on top which was further equipped with a Quartz Thermometer or a thermistor was used. About 18 g trans-HFO-1233 is charged to the ebulliometer and then trans-1,2-DCE was added in small, measured increments. Temperature depression was observed when trans-1,2-DCE was added to trans-HFO-1233, indicating a binary minimum boiling azeotrope was formed. From greater than about 0.01 to about 53 weight percent trans-1,2-DCE, the boiling point of the composition changed by about 0.7° C. or less. The boiling points of the binary mixtures shown in Table 4 changed by less than about 0.3° C. Thus the compositions exhibited azeotrope and/or azeotrope-like properties over these ranges.

TABLE 5 trans-HFO-1233zd/trans-1,2-DCE compositions at ambient pressure

| T(° C.) | Wt. % trans-HFO-1233zd | Wt. % tr-1,2-DCE |
|---|---|---|
| 17.74 (° C.) | 100.00 wt. % | 0.00 wt. % |
| 17.74 (° C.) | 99.68 wt. % | 0.32 wt. % |
| 17.73 (° C.) | 99.35 wt. % | 0.65 wt. % |
| 17.76 (° C.) | 99.03 wt. % | 0.97 wt. % |
| 17.79 (° C.) | 98.72 wt. % | 1.28 wt. % |
| 17.82 (° C.) | 98.40 wt. % | 1.60 wt. % |
| 17.85 (° C.) | 98.08 wt. % | 1.92 wt. % |
| 17.88 (° C.) | 97.77 wt. % | 2.23 wt. % |
| 17.92 (° C.) | 97.46 wt. % | 2.54 wt. % |
| 17.96 (° C.) | 97.15 wt. % | 2.85 wt. % |

Examples 6-23

The general procedure described in examples 1-5 above was repeated for examples 6-23. Azeotrope-like behavior was observed over a given range of component concentrations where the boiling point changed by ≤1° C. The results are summarized below:

| Azeotrope-like mixture | Relative Concentration 1233zd: Other Component(s) (wt. %) | Boiling Point (° C.) @ ambient pressure | Data Table |
|---|---|---|---|
| trans-HFO-1233zd + isohexane | 94.4-99.99/0.01-5.6 | 17.4 ± 1 | 6 |
| trans-HFO-1233zd + ethanol | 85-99.9/0.1-15 | 18.1 ± 1 | 7 |
| trans-HFO-1233zd + isopropanol | 90-99.9/0.1-10 | 17.9 ± 1 | 8 |
| trans-HFO-1233zd + 1-chloropropane | 96-99.9/0.1-4 | 18 ± 1 | 9 |
| trans-HFO-1233zd + 2-chloropropane | 94-99.99/0.01-6 | 17.8 ± 1 | 10 |
| trans-HFO-1233zd + cyclopentene | 95-99.9/0.1-5 | 18.1 ± 1 | 11 |
| trans-HFO-1233zd + cyclopentane | 95-99.9/0.1-5 | 17.5 ± 1 | 12 |
| trans-HFO-1233zd + methylal | 95-99.9/0.1-5 | 17.3 ± 1 | 13 |
| trans-HFO-1233zd + methyl acetate | 90-99.9/0.1-5 | 17.5 ± 1 | 14 |
| trans-HFO-1233zd + HFC-365mfc | 89-99.9/0.1-11 | 17.5 ± 1 | 15 |
| trans-HFO-1233zd + n-hexane | 95-99.99/0.01-5 | 17.4 ± 1 | 16 |
| cis-HFO-1233zd + methanol | 78-99.9/0.1-22 | 35.2 ± 1 | 17 |
| cis-HFO-1233zd + ethanol | 65-99.9/0.1-35 | 37.4 ± 1 | 18 |
| cis-HFO-1233zd + isopropanol | 85-99.99/0.01-15 | 38.1 ± 1 | 19 |
| cis-HFO-1233zd + cyclopentane | 42-99/1-58 | 34.7 ± 1 | 20 |
| cis-HFO-1233zd + trans-1,2-DCE | 42-99.9/0.1-58 | 37 ± 1 | 21 |
| trans-HFO-1233zd + trans-1,2-DCE + n-pentane | 55-99.9/0.05-10/0.05-35 | 17.4 ± 1 | 22 |
| trans-HFO-1233zd + trans-1,2-DCE + methanol | 80-09/0.05-15/0.05-10 | 16.6 ± 1 | 23 |

TABLE 6 trans-HFO-1233zd/isohexane compositions at ambient pressure

| isohexane (wt. %) | trans-1233zd (wt. %) | Boiling Point (° C.) |
| --- | --- | --- |
| 0.0 | 100.0 | 17.5 |
| 0.2 | 99.8 | 17.5 |
| 0.3 | 99.7 | 17.6 |
| 0.5 | 99.5 | 17.6 |
| 0.7 | 99.3 | 17.6 |
| 0.8 | 99.2 | 17.6 |
| 1.0 | 99.0 | 17.7 |
| 1.2 | 98.8 | 17.7 |
| 1.3 | 98.7 | 17.7 |
| 1.5 | 98.5 | 17.8 |
| 1.7 | 98.3 | 17.8 |
| 1.8 | 98.2 | 17.8 |
| 2.0 | 98.0 | 17.8 |
| 2.2 | 97.8 | 17.9 |
| 2.3 | 97.7 | 17.9 |
| 2.5 | 97.5 | 17.9 |
| 2.6 | 97.4 | 18.0 |
| 2.8 | 97.2 | 18.0 |
| 3.0 | 97.0 | 18.0 |
| 3.1 | 96.9 | 18.1 |
| 3.3 | 96.7 | 18.1 |
| 3.4 | 96.6 | 18.1 |
| 3.6 | 96.4 | 18.2 |
| 3.8 | 96.2 | 18.2 |
| 3.9 | 96.1 | 18.2 |
| 4.1 | 95.9 | 18.2 |
| 4.2 | 95.8 | 18.3 |
| 4.4 | 95.6 | 18.3 |
| 4.5 | 95.5 | 18.3 |
| 4.7 | 95.3 | 18.4 |
| 4.9 | 95.1 | 18.4 |
| 5.0 | 95.0 | 18.4 |
| 5.2 | 94.8 | 18.4 |

TABLE 7 trans-HFO-1233zd/ethanol compositions at ambient pressure

| EtOH (wt. %) | trans-1233zd (wt. %) | Boiling Point (° C.) |
| --- | --- | --- |
| 0.0 | 100.0 | 18.1 |
| 0.2 | 99.8 | 18.1 |
| 0.4 | 99.6 | 18.1 |
| 0.6 | 99.4 | 18.1 |
| 0.8 | 99.2 | 18.1 |
| 1.0 | 99.0 | 18.1 |
| 1.2 | 98.8 | 18.1 |
| 1.4 | 98.6 | 18.1 |
| 1.6 | 98.4 | 18.1 |
| 1.8 | 98.2 | 18.2 |
| 2.0 | 98.0 | 18.2 |
| 2.2 | 97.8 | 18.2 |
| 2.4 | 97.6 | 18.1 |
| 2.6 | 97.4 | 18.1 |
| 2.8 | 97.2 | 18.2 |
| 3.0 | 97.0 | 18.2 |
| 3.2 | 96.8 | 18.2 |
| 3.4 | 96.6 | 18.2 |
| 3.6 | 96.4 | 18.2 |
| 3.8 | 96.2 | 18.2 |
| 4.0 | 96.0 | 18.2 |
| 4.1 | 95.9 | 18.2 |
| 4.3 | 95.7 | 18.2 |
| 4.5 | 95.5 | 18.2 |
| 4.7 | 95.3 | 18.2 |
| 4.9 | 95.1 | 18.2 |
| 5.1 | 94.9 | 18.2 |

TABLE 8 trans-HFO-1233zd/isopropanol compositions at ambient pressure

| IPA (wt. %) | trans-1233zd (wt. %) | Boiling Point (° C.) |
| --- | --- | --- |
| 0.0 | 100.0 | 17.9 |
| 0.4 | 99.6 | 17.9 |
| 0.8 | 99.2 | 17.9 |
| 1.2 | 98.8 | 17.9 |
| 1.6 | 98.4 | 17.9 |
| 2.0 | 98.0 | 17.9 |
| 2.4 | 97.6 | 17.9 |
| 2.8 | 97.2 | 18.0 |
| 3.2 | 96.8 | 18.0 |
| 3.5 | 96.5 | 18.1 |
| 3.9 | 96.1 | 18.1 |
| 4.3 | 95.7 | 18.1 |
| 4.7 | 95.3 | 18.2 |
| 5.0 | 95.0 | 18.2 |
| 5.4 | 94.6 | 18.2 |
| 5.8 | 94.2 | 18.3 |
| 6.1 | 93.9 | 18.3 |
| 6.5 | 93.5 | 18.3 |
| 6.9 | 93.1 | 18.3 |
| 7.2 | 92.8 | 18.4 |
| 7.6 | 92.4 | 18.4 |
| 7.9 | 92.1 | 18.4 |
| 8.3 | 91.7 | 18.4 |
| 8.6 | 91.4 | 18.4 |
| 8.9 | 91.1 | 18.5 |
| 9.3 | 90.7 | 18.5 |
| 9.6 | 90.4 | 18.5 |

TABLE 9 trans-HFO-1233zd/1-chloropropane compositions at ambient pressure

| 1-chloropropane (wt. %) | trans-1233zd (wt. %) | Boiling Point (° C.) |
| --- | --- | --- |
| 0.0 | 100.0 | 18.0 |
| 0.2 | 99.8 | 18.0 |
| 0.5 | 99.5 | 18.0 |
| 0.7 | 99.3 | 18.0 |
| 0.9 | 99.1 | 18.0 |
| 1.1 | 98.9 | 18.1 |
| 1.4 | 98.6 | 18.1 |
| 1.6 | 98.4 | 18.2 |
| 1.8 | 98.2 | 18.2 |
| 2.0 | 98.0 | 18.3 |
| 2.3 | 97.7 | 18.3 |
| 2.5 | 97.5 | 18.4 |
| 2.7 | 97.3 | 18.5 |
| 2.9 | 97.1 | 18.5 |
| 3.1 | 96.9 | 18.6 |
| 3.4 | 96.6 | 18.6 |
| 3.6 | 96.4 | 18.6 |
| 3.8 | 96.2 | 18.7 |
| 4.0 | 96.0 | 18.8 |
| 4.2 | 95.8 | 18.8 |
| 4.4 | 95.6 | 18.8 |
| 4.6 | 95.4 | 18.9 |
| 4.9 | 95.1 | 18.9 |
| 5.1 | 94.9 | 19.0 |
| 5.3 | 94.7 | 19.0 |
| 5.5 | 94.5 | 19.1 |
| 5.7 | 94.3 | 19.1 |

TABLE 10 trans-HFO-1233zd/2-chloropropane compositions at ambient pressure

| 2-chloropropane (wt. %) | trans-1233zd (wt. %) | Boiling Point (° C.) |
| --- | --- | --- |
| 0.0 | 100.0 | 17.8 |
| 0.2 | 99.8 | 17.8 |

TABLE 10-continued trans-HFO-1233zd/2-chloropropane compositions at ambient pressure

| 2-chloropropane (wt. %) | trans-1233zd (wt. %) | Boiling Point (° C.) |
| --- | --- | --- |
| 0.4 | 99.6 | 17.8 |
| 0.7 | 99.3 | 17.8 |
| 0.9 | 99.1 | 17.8 |
| 1.1 | 98.9 | 17.9 |
| 1.3 | 98.7 | 17.9 |
| 1.5 | 98.5 | 17.9 |
| 1.8 | 98.2 | 17.9 |
| 2.0 | 98.0 | 18.0 |
| 2.2 | 97.8 | 18.0 |
| 2.4 | 97.6 | 18.0 |
| 2.6 | 97.4 | 18.0 |
| 2.8 | 97.2 | 18.0 |
| 3.0 | 97.0 | 18.0 |
| 3.3 | 96.7 | 18.0 |
| 3.5 | 96.5 | 18.1 |
| 3.7 | 96.3 | 18.1 |
| 3.9 | 96.1 | 18.1 |
| 4.1 | 95.9 | 18.1 |
| 4.3 | 95.7 | 18.1 |
| 4.5 | 95.5 | 18.1 |
| 4.7 | 95.3 | 18.2 |
| 4.9 | 95.1 | 18.2 |
| 5.1 | 94.9 | 18.2 |
| 5.3 | 94.7 | 18.2 |
| 5.5 | 94.5 | 18.2 |
| 5.7 | 94.3 | 18.2 |
| 5.9 | 94.1 | 18.2 |
| 6.1 | 93.9 | 18.2 |
| 6.3 | 93.7 | 18.3 |

TABLE 11 trans-HFO-1233zd/cyclopentene compositions at ambient pressure

| cyclopentene (wt. %) | trans-1233zd (wt. %) | Boiling Point (° C.) |
| --- | --- | --- |
| 0.0 | 100.0 | 17.8 |
| 0.2 | 99.8 | 17.8 |
| 0.4 | 99.6 | 17.8 |
| 0.6 | 99.4 | 17.9 |
| 0.8 | 99.2 | 17.9 |
| 1.0 | 99.0 | 17.9 |
| 1.2 | 98.8 | 18.0 |
| 1.4 | 98.6 | 18.0 |
| 1.6 | 98.4 | 18.0 |
| 1.8 | 98.2 | 18.1 |
| 2.0 | 98.0 | 18.1 |
| 2.2 | 97.8 | 18.1 |
| 2.4 | 97.6 | 18.2 |
| 2.5 | 97.5 | 18.2 |
| 2.7 | 97.3 | 18.2 |
| 2.9 | 97.1 | 18.3 |
| 3.1 | 96.9 | 18.3 |
| 3.3 | 96.7 | 18.3 |
| 3.5 | 96.5 | 18.3 |
| 3.7 | 96.3 | 18.4 |
| 3.9 | 96.1 | 18.4 |
| 4.1 | 95.9 | 18.4 |
| 4.2 | 95.8 | 18.4 |
| 4.4 | 95.6 | 18.5 |
| 4.6 | 95.4 | 18.5 |
| 4.8 | 95.2 | 18.5 |

TABLE 12 trans-HFO-1233zd/cyclopentane compositions at ambient pressure

| cyclopentane (wt. %) | trans-1233zd (wt. %) | Boiling Point (° C.) |
| --- | --- | --- |
| 0.0 | 100.0 | 17.6 |
| 0.2 | 99.8 | 17.6 |

TABLE 12-continued trans-HFO-1233zd/cyclopentane compositions at ambient pressure

| cyclopentane (wt. %) | trans-1233zd (wt. %) | Boiling Point (° C.) |
| --- | --- | --- |
| 0.4 | 99.6 | 17.7 |
| 0.6 | 99.4 | 17.7 |
| 1.0 | 99.0 | 17.8 |
| 1.3 | 98.7 | 17.8 |
| 1.7 | 98.3 | 17.8 |
| 2.1 | 97.9 | 17.8 |
| 2.5 | 97.5 | 17.9 |
| 2.8 | 97.2 | 17.9 |
| 3.2 | 96.8 | 18.0 |
| 3.6 | 96.4 | 18.1 |
| 3.9 | 96.1 | 18.1 |
| 4.3 | 95.7 | 18.2 |
| 4.6 | 95.4 | 18.2 |
| 5.0 | 95.0 | 18.3 |
| 5.3 | 94.7 | 18.3 |
| 5.7 | 94.3 | 18.4 |

TABLE 13 trans-HFO-1233zd/methylal compositions at ambient pressure

| methylal (wt. %) | trans-1233zd (wt. %) | Boiling Point (° C.) |
| --- | --- | --- |
| 0.0 | 100.0 | 17.5 |
| 0.2 | 99.8 | 17.5 |
| 0.4 | 99.6 | 17.5 |
| 0.7 | 99.3 | 17.3 |
| 0.9 | 99.1 | 17.4 |
| 1.1 | 98.9 | 17.4 |
| 1.3 | 98.7 | 17.5 |
| 1.5 | 98.5 | 17.6 |
| 1.8 | 98.2 | 17.7 |
| 2.0 | 98.0 | 17.8 |
| 2.2 | 97.8 | 17.9 |
| 2.4 | 97.6 | 18.0 |
| 2.6 | 97.4 | 18.1 |
| 2.8 | 97.2 | 18.2 |
| 3.1 | 96.9 | 18.2 |
| 3.3 | 96.7 | 18.3 |
| 3.5 | 96.5 | 18.4 |
| 3.7 | 96.3 | 18.5 |
| 3.9 | 96.1 | 18.6 |
| 4.1 | 95.9 | 18.6 |
| 4.3 | 95.7 | 18.7 |
| 4.5 | 95.5 | 18.8 |
| 4.7 | 95.3 | 18.8 |
| 4.9 | 95.1 | 18.9 |
| 5.1 | 94.9 | 18.9 |

TABLE 14 trans-HFO-1233zd/methyl acetate compositions at ambient pressure

| Me-Acetate (wt. %) | trans-1233zd (wt. %) | Boiling Point (° C.) |
| --- | --- | --- |
| 0.0 | 100.0 | 17.6 |
| 0.2 | 99.8 | 17.7 |
| 0.4 | 99.6 | 17.7 |
| 0.7 | 99.3 | 17.8 |
| 0.9 | 99.1 | 17.9 |
| 1.1 | 98.9 | 18.0 |
| 1.3 | 98.7 | 18.0 |
| 1.5 | 98.5 | 18.1 |
| 1.8 | 98.2 | 18.2 |
| 2.0 | 98.0 | 18.3 |
| 2.2 | 97.8 | 18.3 |
| 2.4 | 97.6 | 18.4 |
| 2.6 | 97.4 | 18.4 |
| 2.8 | 97.2 | 18.5 |
| 3.1 | 96.9 | 18.6 |
| 3.3 | 96.7 | 18.6 |

TABLE 14-continued trans-HFO-1233zd/methyl acetate compositions at ambient pressure

| Me-Acetate (wt. %) | trans-1233zd (wt. %) | Boiling Point (° C.) |
|---|---|---|
| 3.5 | 96.5 | 18.7 |
| 3.7 | 96.3 | 18.7 |

TABLE 15 trans-HFO-1233zd/HFC-365mfc compositions at ambient pressure

| HFC-365mfc (wt. %) | trans-1233zd (wt. %) | Boiling Point (° C.) |
|---|---|---|
| 0.0 | 100.0 | 17.6 |
| 0.3 | 99.7 | 17.6 |
| 0.6 | 99.4 | 17.6 |
| 1.0 | 99.0 | 17.6 |
| 1.3 | 98.7 | 17.7 |
| 1.6 | 98.4 | 17.7 |
| 1.9 | 98.1 | 17.7 |
| 2.2 | 97.8 | 17.7 |
| 2.5 | 97.5 | 17.8 |
| 2.9 | 97.1 | 17.8 |
| 3.2 | 96.8 | 17.8 |
| 3.5 | 96.5 | 17.8 |
| 3.8 | 96.2 | 17.9 |
| 4.1 | 95.9 | 17.9 |
| 4.4 | 95.6 | 17.9 |
| 4.7 | 95.3 | 17.9 |
| 5.0 | 95.0 | 18.0 |
| 5.3 | 94.7 | 18.0 |
| 5.5 | 94.5 | 18.0 |
| 5.8 | 94.2 | 18.0 |
| 6.1 | 93.9 | 18.1 |
| 6.4 | 93.6 | 18.1 |
| 6.7 | 93.3 | 18.1 |
| 7.0 | 93.0 | 18.1 |
| 7.3 | 92.7 | 18.1 |
| 7.5 | 92.5 | 18.2 |
| 7.8 | 92.2 | 18.2 |
| 8.1 | 91.9 | 18.2 |
| 8.4 | 91.6 | 18.2 |

TABLE 16 trans-HFO-1233zd/n-hexane compositions at ambient pressure

| n-hexane (wt. %) | trans-1233zd (wt. %) | Boiling Point (° C.) |
|---|---|---|
| 0.0 | 100.0 | 17.3 |
| 0.2 | 99.8 | 17.3 |
| 0.3 | 99.7 | 17.4 |
| 0.5 | 99.5 | 17.4 |
| 0.7 | 99.3 | 17.4 |
| 0.9 | 99.1 | 17.5 |
| 1.0 | 99.0 | 17.5 |
| 1.2 | 98.8 | 17.5 |
| 1.4 | 98.6 | 17.6 |
| 1.5 | 98.5 | 17.6 |
| 1.7 | 98.3 | 17.6 |
| 1.9 | 98.1 | 17.7 |
| 2.0 | 98.0 | 17.7 |

TABLE 17 cis-HFO-1233zd/methanol compositions at ambient pressure

| methanol (wt. %) | cis-1233zd (wt. %) | Boiling Point (° C.) |
|---|---|---|
| 0.0 | 100.0 | 37.5 |
| 0.6 | 99.4 | 36.6 |
| 1.2 | 98.8 | 35.8 |
| 1.8 | 98.2 | 35.5 |

TABLE 17-continued cis-HFO-1233zd/methanol compositions at ambient pressure

| methanol (wt. %) | cis-1233zd (wt. %) | Boiling Point (° C.) |
|---|---|---|
| 2.4 | 97.6 | 35.3 |
| 3.0 | 97.0 | 35.2 |
| 3.6 | 96.4 | 35.2 |
| 4.2 | 95.8 | 35.2 |
| 4.7 | 95.3 | 35.2 |
| 5.3 | 94.7 | 35.2 |
| 5.9 | 94.1 | 35.3 |
| 6.9 | 93.1 | 35.4 |
| 8.0 | 92.0 | 35.4 |
| 9.1 | 90.9 | 35.5 |
| 10.1 | 89.9 | 35.5 |
| 11.1 | 88.9 | 35.6 |
| 12.0 | 88.0 | 35.6 |
| 13.0 | 87.0 | 35.6 |
| 13.9 | 86.1 | 35.7 |
| 14.8 | 85.2 | 35.7 |
| 15.7 | 84.3 | 35.8 |
| 16.6 | 83.4 | 35.8 |
| 17.5 | 82.5 | 35.9 |
| 18.3 | 81.7 | 35.9 |
| 19.1 | 80.9 | 36.0 |
| 19.9 | 80.1 | 36.0 |
| 20.7 | 79.3 | 36.1 |
| 21.5 | 78.5 | 36.1 |
| 22.2 | 77.8 | 36.2 |
| 23.0 | 77.0 | 36.2 |
| 23.7 | 76.3 | 36.3 |
| 24.4 | 75.6 | 36.3 |
| 25.1 | 74.9 | 36.3 |
| 25.8 | 74.2 | 36.4 |
| 26.5 | 73.5 | 36.4 |
| 27.2 | 72.8 | 36.5 |
| 27.8 | 72.2 | 36.5 |

TABLE 18 cis-HFO-1233zd/ethanol compositions at ambient pressure

| ethanol (wt. %) | cis-1233zd (wt. %) | Boiling Point (° C.) |
|---|---|---|
| 0.0 | 100.0 | 37.8 |
| 0.6 | 99.4 | 37.7 |
| 1.2 | 98.8 | 37.6 |
| 1.8 | 98.2 | 37.6 |
| 2.4 | 97.6 | 37.6 |
| 3.0 | 97.0 | 37.6 |
| 3.6 | 96.4 | 37.5 |
| 4.2 | 95.8 | 37.4 |
| 4.7 | 95.3 | 37.4 |
| 5.9 | 94.1 | 37.5 |
| 6.9 | 93.1 | 37.5 |
| 8.0 | 92.0 | 37.4 |
| 9.1 | 90.9 | 37.5 |
| 10.1 | 89.9 | 37.5 |
| 11.1 | 88.9 | 37.6 |
| 12.0 | 88.0 | 37.5 |
| 13.0 | 87.0 | 37.6 |
| 13.9 | 86.1 | 37.5 |
| 14.8 | 85.2 | 37.6 |
| 15.7 | 84.3 | 37.7 |
| 16.6 | 83.4 | 37.7 |
| 17.5 | 82.5 | 37.7 |
| 18.3 | 81.7 | 37.7 |
| 19.1 | 80.9 | 37.7 |
| 19.9 | 80.1 | 37.6 |
| 20.7 | 79.3 | 37.6 |
| 21.5 | 78.5 | 37.7 |
| 22.2 | 77.8 | 37.7 |
| 23.0 | 77.0 | 37.8 |
| 23.7 | 76.3 | 37.8 |
| 24.4 | 75.6 | 37.8 |
| 25.1 | 74.9 | 37.8 |
| 25.8 | 74.2 | 37.8 |

TABLE 18-continued cis-HFO-1233zd/ethanol compositions at ambient pressure

| ethanol (wt. %) | cis-1233zd (wt. %) | Boiling Point (° C.) |
| --- | --- | --- |
| 26.5 | 73.5 | 37.8 |
| 27.2 | 72.8 | 37.8 |
| 27.8 | 72.2 | 37.9 |
| 28.5 | 71.5 | 37.9 |
| 29.1 | 70.9 | 37.9 |

TABLE 19 cis-HFO-1233zd/isopropanol compositions at ambient pressure

| IPA (wt. %) | cis-1233zd (wt. %) | Boiling Point (° C.) |
| --- | --- | --- |
| 0.0 | 100.0 | 38.1 |
| 0.6 | 99.4 | 38.1 |
| 1.2 | 98.8 | 38.1 |
| 1.8 | 98.2 | 38.2 |
| 3.0 | 97.0 | 38.2 |
| 4.1 | 95.9 | 38.3 |
| 5.3 | 94.7 | 38.4 |
| 6.4 | 93.6 | 38.5 |
| 7.4 | 92.6 | 38.6 |
| 8.5 | 91.5 | 38.6 |
| 9.5 | 90.5 | 38.7 |
| 10.5 | 89.5 | 38.7 |
| 11.5 | 88.5 | 38.8 |
| 12.4 | 87.6 | 38.8 |
| 13.4 | 86.6 | 38.8 |

TABLE 20 cis-HFO-1233zd/cyclopentane compositions at ambient pressure

| cyclopentane (wt. %) | cis-1233zd (wt. %) | Boiling Point (° C.) |
| --- | --- | --- |
| 0.0 | 100.0 | 37.5 |
| 1.2 | 98.8 | 37.1 |
| 2.3 | 97.7 | 36.6 |
| 3.4 | 96.6 | 36.3 |
| 4.5 | 95.5 | 36.0 |
| 5.6 | 94.4 | 35.8 |
| 6.6 | 93.4 | 35.6 |
| 7.6 | 92.4 | 35.5 |
| 8.6 | 91.4 | 35.3 |
| 9.6 | 90.4 | 35.3 |
| 10.6 | 89.4 | 35.2 |
| 11.5 | 88.5 | 35.1 |
| 12.4 | 87.6 | 35.0 |
| 13.3 | 86.7 | 35.0 |
| 14.2 | 85.8 | 35.0 |
| 15.1 | 84.9 | 35.0 |
| 15.9 | 84.1 | 34.9 |
| 16.7 | 83.3 | 34.9 |
| 17.6 | 82.4 | 34.9 |
| 18.3 | 81.7 | 34.9 |
| 19.1 | 80.9 | 34.9 |
| 19.9 | 80.1 | 34.9 |
| 20.6 | 79.4 | 34.9 |
| 21.4 | 78.6 | 34.9 |
| 22.1 | 77.9 | 34.8 |
| 22.8 | 77.2 | 34.8 |
| 23.5 | 76.5 | 34.7 |
| 24.2 | 75.8 | 34.7 |
| 24.9 | 75.1 | 34.7 |
| 25.5 | 74.5 | 34.7 |
| 26.2 | 73.8 | 34.7 |
| 26.8 | 73.2 | 34.8 |
| 27.5 | 72.5 | 34.8 |
| 28.1 | 71.9 | 34.8 |
| 28.7 | 71.3 | 34.8 |
| 29.3 | 70.7 | 34.8 |
| 29.9 | 70.1 | 34.8 |

TABLE 21 cis-HFO-1233zd/trans-1,2-DCE compositions at ambient pressure

| trans-1,2-DCE (wt. %) | cis-1233zd (wt. %) | Boiling Point (° C.) |
| --- | --- | --- |
| 0.0 | 100.0 | 37.8 |
| 1.0 | 99.0 | 37.8 |
| 1.9 | 98.1 | 37.8 |
| 3.8 | 96.2 | 37.7 |
| 7.3 | 92.7 | 37.5 |
| 10.6 | 89.4 | 37.4 |
| 13.7 | 86.3 | 37.2 |
| 16.5 | 83.5 | 37.1 |
| 19.2 | 80.8 | 37.1 |
| 21.7 | 78.3 | 37.0 |
| 24.1 | 75.9 | 37.0 |
| 26.3 | 73.7 | 37.0 |
| 28.4 | 71.6 | 37.1 |
| 30.3 | 69.7 | 37.1 |
| 32.2 | 67.8 | 37.1 |
| 34.0 | 66.0 | 37.1 |
| 35.7 | 64.3 | 37.1 |
| 37.3 | 62.7 | 37.1 |
| 38.8 | 61.2 | 37.1 |
| 40.2 | 59.8 | 37.1 |
| 41.6 | 58.4 | 37.2 |
| 42.9 | 57.1 | 37.2 |
| 44.2 | 55.8 | 37.2 |
| 45.4 | 54.6 | 37.3 |
| 46.6 | 53.4 | 37.3 |
| 47.7 | 52.3 | 37.3 |
| 48.2 | 51.8 | 37.4 |
| 48.7 | 51.3 | 37.4 |
| 49.2 | 50.8 | 37.4 |
| 49.7 | 50.3 | 37.4 |
| 50.2 | 49.8 | 37.4 |
| 50.7 | 49.3 | 37.5 |
| 51.2 | 48.8 | 37.5 |
| 51.7 | 48.3 | 37.5 |
| 52.1 | 47.9 | 37.5 |
| 52.6 | 47.4 | 37.6 |
| 53.0 | 47.0 | 37.6 |
| 53.4 | 46.6 | 37.6 |
| 53.9 | 46.1 | 37.6 |
| 54.3 | 45.7 | 37.6 |
| 54.7 | 45.3 | 37.6 |
| 55.1 | 44.9 | 37.6 |

TABLE 22 trans-HFO-1233zd/methanol/n-pentane compositions at ambient pressure

| n-pentane (wt. %) | trans-1233zd (wt. %) | methanol (wt. %) | Boiling Point (° C.) |
| --- | --- | --- | --- |
| 0.0 | 98.0 | 2.0 | 17.1 |
| 0.2 | 97.8 | 2.0 | 17.1 |
| 0.3 | 97.7 | 2.0 | 17.1 |
| 0.5 | 97.5 | 2.0 | 17.1 |
| 0.6 | 97.4 | 2.0 | 17.1 |
| 0.8 | 97.2 | 2.0 | 17.1 |
| 1.0 | 97.1 | 2.0 | 17.1 |
| 1.1 | 96.9 | 2.0 | 17.1 |
| 1.3 | 96.7 | 2.0 | 17.1 |
| 1.4 | 96.6 | 2.0 | 17.1 |
| 1.6 | 96.4 | 2.0 | 17.1 |
| 1.7 | 96.3 | 2.0 | 17.1 |
| 1.9 | 96.1 | 2.0 | 17.0 |
| 2.0 | 96.0 | 2.0 | 17.0 |
| 2.2 | 95.9 | 2.0 | 17.0 |
| 2.3 | 95.7 | 2.0 | 17.0 |
| 2.5 | 95.6 | 2.0 | 17.0 |
| 2.6 | 95.4 | 1.9 | 17.0 |
| 2.8 | 95.3 | 1.9 | 17.0 |
| 2.9 | 95.1 | 1.9 | 17.0 |
| 3.1 | 95.0 | 1.9 | 17.0 |
| 3.2 | 94.8 | 1.9 | 17.0 |

TABLE 22-continued trans-HFO-1233zd/methanol/n-pentane compositions at ambient pressure

| n-pentane (wt. %) | trans-1233zd (wt. %) | methanol (wt. %) | Boiling Point (° C.) |
|---|---|---|---|
| 3.4 | 94.7 | 1.9 | 17.0 |
| 3.5 | 94.6 | 1.9 | 17.0 |
| 3.6 | 94.4 | 1.9 | 17.0 |
| 3.8 | 94.3 | 1.9 | 17.0 |
| 3.9 | 94.2 | 1.9 | 17.0 |
| 4.1 | 94.0 | 1.9 | 17.0 |
| 4.2 | 93.9 | 1.9 | 17.0 |
| 4.3 | 93.7 | 1.9 | 17.0 |
| 4.5 | 93.6 | 1.9 | 17.0 |
| 4.6 | 93.5 | 1.9 | 17.0 |
| 4.7 | 93.4 | 1.9 | 17.0 |
| 4.9 | 93.2 | 1.9 | 17.0 |
| 5.0 | 93.1 | 1.9 | 17.0 |
| 5.1 | 93.0 | 1.9 | 17.0 |
| 5.3 | 92.8 | 1.9 | 17.0 |
| 5.4 | 92.7 | 1.9 | 17.0 |
| 5.5 | 92.6 | 1.9 | 17.0 |
| 5.7 | 92.4 | 1.9 | 17.0 |
| 5.8 | 92.3 | 1.9 | 17.0 |
| 5.9 | 92.2 | 1.9 | 17.0 |
| 6.0 | 92.1 | 1.9 | 17.0 |
| 6.2 | 91.9 | 1.9 | 17.1 |
| 6.3 | 91.8 | 1.9 | 17.1 |
| 6.4 | 91.7 | 1.9 | 17.1 |
| 6.5 | 91.6 | 1.9 | 17.1 |
| 6.7 | 91.5 | 1.9 | 17.1 |
| 6.8 | 91.3 | 1.9 | 17.1 |
| 6.9 | 91.2 | 1.9 | 17.1 |
| 7.0 | 91.1 | 1.9 | 17.1 |
| 7.2 | 91.0 | 1.9 | 17.1 |
| 7.3 | 90.9 | 1.9 | 17.1 |
| 7.4 | 90.8 | 1.9 | 17.1 |
| 7.5 | 90.6 | 1.8 | 17.1 |
| 7.6 | 90.5 | 1.8 | 17.1 |
| 7.8 | 90.4 | 1.8 | 17.1 |
| 7.9 | 90.3 | 1.8 | 17.1 |
| 8.0 | 90.2 | 1.8 | 17.1 |
| 8.1 | 90.1 | 1.8 | 17.1 |
| 8.2 | 90.0 | 1.8 | 17.1 |
| 8.3 | 89.8 | 1.8 | 17.1 |
| 8.4 | 89.7 | 1.8 | 17.1 |
| 8.6 | 89.6 | 1.8 | 17.1 |
| 8.7 | 89.5 | 1.8 | 17.1 |
| 8.8 | 89.4 | 1.8 | 17.1 |
| 8.9 | 89.3 | 1.8 | 17.1 |
| 9.0 | 89.2 | 1.8 | 17.1 |
| 9.1 | 89.1 | 1.8 | 17.1 |
| 9.2 | 89.0 | 1.8 | 17.1 |
| 9.3 | 88.9 | 1.8 | 17.1 |
| 9.4 | 88.8 | 1.8 | 17.1 |
| 9.5 | 88.6 | 1.8 | 17.1 |
| 9.6 | 88.5 | 1.8 | 17.1 |
| 9.8 | 88.4 | 1.8 | 17.2 |
| 9.9 | 88.3 | 1.8 | 17.2 |
| 10.1 | 88.1 | 1.8 | 17.2 |
| 10.3 | 87.9 | 1.8 | 17.2 |
| 10.5 | 87.7 | 1.8 | 17.2 |
| 10.7 | 87.5 | 1.8 | 17.2 |
| 10.9 | 87.3 | 1.8 | 17.2 |
| 11.1 | 87.1 | 1.8 | 17.2 |
| 11.3 | 86.9 | 1.8 | 17.2 |
| 11.5 | 86.7 | 1.8 | 17.2 |
| 11.7 | 86.6 | 1.8 | 17.2 |
| 11.9 | 86.4 | 1.8 | 17.2 |
| 12.1 | 86.2 | 1.8 | 17.3 |
| 12.2 | 86.0 | 1.8 | 17.3 |
| 12.4 | 85.8 | 1.8 | 17.3 |
| 12.6 | 85.6 | 1.7 | 17.3 |
| 12.8 | 85.5 | 1.7 | 17.3 |
| 13.0 | 85.3 | 1.7 | 17.3 |
| 13.2 | 85.1 | 1.7 | 17.3 |
| 13.3 | 84.9 | 1.7 | 17.3 |
| 13.5 | 84.8 | 1.7 | 17.4 |
| 13.7 | 84.6 | 1.7 | 17.4 |
| 13.9 | 84.4 | 1.7 | 17.4 |
| 14.0 | 84.3 | 1.7 | 17.4 |
| 14.2 | 84.1 | 1.7 | 17.4 |
| 14.4 | 83.9 | 1.7 | 17.4 |
| 14.5 | 83.8 | 1.7 | 17.4 |
| 14.7 | 83.6 | 1.7 | 17.4 |
| 14.9 | 83.4 | 1.7 | 17.5 |
| 15.0 | 83.3 | 1.7 | 17.5 |
| 15.2 | 83.1 | 1.7 | 17.5 |
| 15.3 | 83.0 | 1.7 | 17.5 |
| 15.5 | 82.8 | 1.7 | 17.5 |
| 15.6 | 82.7 | 1.7 | 17.5 |

TABLE 23 trans-HFO-1233zd/methanol/trans-1,2-DCE compositions at ambient pressure

| trans-1,2-DCE (wt. %) | trans-1233zd/methanol (in 98:2 wt. ratio) (wt. %) | Boiling Point (° C.) |
|---|---|---|
| 0.0 | 100.0 | 16.7 |
| 0.3 | 99.7 | 16.7 |
| 0.6 | 99.4 | 16.8 |
| 1.0 | 99.0 | 16.8 |
| 1.3 | 98.7 | 16.8 |
| 1.6 | 98.4 | 16.9 |
| 1.9 | 98.1 | 16.9 |
| 2.2 | 97.8 | 17.0 |
| 2.5 | 97.5 | 17.0 |
| 2.9 | 97.1 | 17.1 |
| 3.2 | 96.8 | 17.1 |
| 3.5 | 96.5 | 17.1 |
| 3.8 | 96.2 | 17.2 |
| 4.1 | 95.9 | 17.2 |
| 4.4 | 95.6 | 17.3 |
| 4.7 | 95.3 | 17.3 |
| 5.0 | 95.0 | 17.4 |
| 5.3 | 94.7 | 17.4 |
| 5.5 | 94.5 | 17.4 |
| 5.8 | 94.2 | 17.5 |
| 6.1 | 93.9 | 17.5 |
| 6.4 | 93.6 | 17.6 |
| 6.7 | 93.3 | 17.6 |

Example 24

An ebulliometer consisting of vacuum jacketed tube with a condenser on top which was further equipped with a Quartz Thermometer was used. About 10 cc of trans-HFO-1233zd was charged to the ebulliometer and then nitromethane was added in small, measured increments. Temperature depression was observed when nitromethane was added, indicating a binary azeotrope-like composition had been formed.

| Temp (° C.) | Wt. % trans-1233zd | Wt. % Nitromethane |
|---|---|---|
| 17.6 | 100.0 | 0.0 |
| 17.7 | 99.7 | 0.3 |
| 17.8 | 99.4 | 0.6 |
| 17.9 | 99.1 | 0.9 |
| 18.0 | 98.8 | 1.2 |

Example 25

An ebulliometer consisting of vacuum jacketed tube with a condenser on top which was further equipped with a Quartz Thermometer was used. About 10 cc of trans-HFO-1233zd was charged to the ebulliometer and then water was added in small, measured increments. Temperature depression was observed when water was added, indicating a binary minimum boiling azeotrope had been formed. From greater than 0 to about 30 weight percent water, the boiling point of the composition changes less than about 0.5° C. at ambient pressure.

| Temp (° C.) | Wt. % trans-1233zd | Wt. % Water |
|---|---|---|
| 17.9 | 100 | 0 |
| 17.7 | 99.7 | 1.4 |
| 17.5 | 98.6 | 2.6 |
| 17.5 | 95.8 | 5.3 |
| 17.4 | 93.2 | 7.9 |
| 17.4 | 90.7 | 10.3 |
| 17.4 | 87.5 | 13.6 |
| 17.4 | 84.4 | 16.5 |
| 17.4 | 81.6 | 19.3 |
| 17.4 | 79.0 | 21.9 |
| 17.4 | 76.5 | 24.4 |
| 17.4 | 74.2 | 26.7 |
| 17.4 | 72.0 | 28.8 |
| 17.4 | 69.9 | 30.9 |

Example 26

An ebulliometer consisting of vacuum jacketed tube with a condenser on top which is further equipped with a Quartz Thermometer is used. An amount of cis-HFO-1233zd is charged to the ebulliometer and then nitromethane is added in small, measured increments. Temperature depression is observed when nitromethane is added to cis-HFO-1233, indicating a binary minimum boiling azeotrope is formed. The compositions exhibit azeotrope and/or azeotrope-like properties over a range of about 95 to 99.9 weight percent cis-1233zd and about 0.1 to about 5 weight percent nitromethane. More pronounced azeotrope and/or azeotrope-like properties occur over a range of about 97 to 99.9 weight percent cis-1233zd and about 0.1 to about 3 weight percent nitromethane; and even more pronounced over a range of about 99 to 99.9 weight percent cis-1233zd and about 0.1 to about 1 weight percent nitromethane.

Example 27

An ebulliometer consisting of vacuum jacketed tube with a condenser on top which is further equipped with a Quartz Thermometer is used. An amount of cis-HFO-1233zd is charged to the ebulliometer and then n-pentane is added in small, measured increments. Temperature depression is observed when n-pentane is added to cis-HFO-1233, indicating a binary minimum boiling azeotrope is formed. The compositions exhibit azeotrope and/or azeotrope-like properties over a range of about 20 to 99.5 weight percent cis-1233zd and about 0.5 to about 80 weight percent n-pentane. More pronounced azeotrope and/or azeotrope-like properties occur over a range of about 50 to 99.5 weight percent cis-1233zd and about 0.5 to about 50 weight percent n-pentane; and even more pronounced over a range of about 60 to 99.5 weight percent cis-1233zd and about 0.5 to about 40 weight percent n-pentane.

Example 28

An ebulliometer consisting of vacuum jacketed tube with a condenser on top which is further equipped with a Quartz Thermometer is used. An amount of cis-HFO-1233zd is charged to the ebulliometer and then neopentane is added in small, measured increments. Temperature depression is observed when neopentane is added to cis-HFO-1233, indicating a binary minimum boiling azeotrope is formed. The compositions exhibit azeotrope and/or azeotrope-like properties over a range of about 5 to 50 weight percent cis-1233zd and about 50 to about 95 weight percent neopentane. More pronounced azeotrope and/or azeotrope-like properties occur over a range of about 20 to 45 weight percent cis-1233zd and about 55 to about 80 weight percent neopentane; and even more pronounced over a range of about 30 to 40 weight percent cis-1233zd and about 60 to about 70 weight percent neopentane.

Example 29

An ebulliometer consisting of vacuum jacketed tube with a condenser on top which is further equipped with a Quartz Thermometer is used. An amount of cis-HFO-1233zd is charged to the ebulliometer and then n-hexane is added in small, measured increments. Temperature depression is observed when n-hexane is added to cis-HFO-1233, indicating a binary minimum boiling azeotrope is formed. The compositions exhibit azeotrope and/or azeotrope-like properties over a range of about 80 to 99.5 weight percent cis-1233zd and about 0.5 to about 20 weight percent n-hexane. More pronounced azeotrope and/or azeotrope-like properties occur over a range of about 90 to 99.5 weight percent cis-1233zd and about 0.5 to about 10 weight percent n-hexane; and even more pronounced over a range of about 95 to 99.5 weight percent cis-1233zd and about 0.5 to about 5 weight percent n-hexane.

Example 30

An ebulliometer consisting of vacuum jacketed tube with a condenser on top which is further equipped with a Quartz Thermometer is used. An amount of cis-HFO-1233zd is charged to the ebulliometer and then isohexane is added in small, measured increments. Temperature depression is observed when isohexane is added to cis-HFO-1233, indicating a binary minimum boiling azeotrope is formed. The compositions exhibit azeotrope and/or azeotrope-like properties over a range of about 70 to 99.5 weight percent cis-1233zd and about 0.5 to about 30 weight percent isohexane. More pronounced azeotrope and/or azeotrope-like properties occur over a range of about 85 to 99.5 weight percent cis-1233zd and about 0.5 to about 15 weight percent isohexane; and even more pronounced over a range of about 93 to 99.5 weight percent cis-1233zd and about 0.5 to about 7 weight percent isohexane.

Example 31

An azeotrope-like mixture containing 98% by weight trans-HFO-1233zd with about 2% by weight methanol is loaded into an aerosol can. An aerosol valve is crimped into place and HFC-134a is added through the valve to achieve a pressure in the can of about 20 PSIG. The mixture is then sprayed onto surface demonstrating that the azeotropic mixture is useful as an aerosol.

Examples 32-57

The steps of Example 31 are generally repeated for Examples 32-57, except that the azeotrope-like mixture identified in the Table below is used instead of trans-HFO-1233zd and methanol. Optionally, the aerosols have a different co-aerosol agent or no co-aerosol agent, and optionally have at least one active ingredient selected from the group consisting of deodorants, perfumes, hair sprays, cleaning solvents, lubricants, insecticides, and medicinal materials. Similar results are demonstrated.

| Example No. | Azeotrope-like Composition | Forms Aerosol |
|---|---|---|
| 32 | trans-1233zd + trans-1,2-DCE | Yes |
| 33 | trans-1233zd + n-pentane | Yes |
| 34 | trans-1233zd + isohexane | Yes |
| 35 | trans-1233zd + neopentane | Yes |
| 36 | trans-1233zd + methanol/n-pentane | Yes |
| 37 | trans-1233zd + methanol/trans-1,2-DCE | Yes |
| 38 | trans-1233zd + ethanol | Yes |
| 39 | trans-1233zd + isopropanol | Yes |
| 40 | trans-1233zd + 1-chloropropane | Yes |
| 41 | trans-1233zd + 2-chloropropane | Yes |
| 42 | trans-1233zd + cyclopentane | Yes |
| 43 | trans-1233zd + cyclopentene | Yes |
| 44 | trans-1233zd + methylal | Yes |
| 45 | trans-1233zd + methyl acetate | Yes |
| 46 | trans-1233zd + n-hexane | Yes |
| 47 | trans-1233zd + nitromethane | Yes |
| 48 | cis-1233zd + methanol | Yes |
| 49 | cis-1233zd + ethanol | Yes |
| 50 | cis-1233zd + isopropanol | Yes |
| 51 | cis-1233zd + n-hexane | Yes |
| 52 | cis-1233zd + isohexane | Yes |
| 53 | cis-1233zd + cyclopentane | Yes |
| 54 | cis-1233zd + n-pentane | Yes |
| 55 | cis-1233zd + nitromethane | Yes |
| 56 | cis-1233zd + trans-1,2-DCE | Yes |
| 57 | cis-1233zd + neopentane | Yes |

Example 58

A mixture containing 98% by weight trans-HFO-1233zd with about 2% by weight methanol is loaded into an aerosol can. An aerosol valve is crimped into place and HFC-134a is added through the valve to achieve a pressure in the can of about 20 PSIG. The mixture is then sprayed onto a metal coupon soiled with solder flux. The flux is removed and the coupon is visually clean.

Examples 59-84

For Examples 59-84, the steps of Example 58 are generally repeated, except that the azeotrope-like mixture identified in the Table below is used instead of trans-HFO-1233zd and methanol, and instead of HFC-134a, a different co-aerosol or no co-aerosol is used. Optionally, the method of applying the azeotropic mixture as a cleaning agent is vapor degreasing or wiping instead of spraying. Optionally, the azeotropic mixture cleaning agent is applied neat. Optionally, the material to be cleaned was changed from solder flux to a mineral oil, silicon oil, or other lubricant. Similar results are demonstrated in each case.

| Example No. | Azeotrope-like Composition | Visually Clean |
|---|---|---|
| 59 | trans-1233zd + trans-1,2-DCE | Yes |
| 60 | trans-1233zd + n-pentane | Yes |
| 61 | trans-1233zd + isohexane | Yes |
| 62 | trans-1233zd + neopentane | Yes |
| 63 | trans-1233zd + methanol/n-pentane | Yes |
| 64 | trans-1233zd + methanol/trans-1,2-DCE | Yes |
| 65 | trans-1233zd + ethanol | Yes |
| 66 | trans-1233zd + isopropanol | Yes |
| 67 | trans-1233zd + 1-chloropropane | Yes |
| 68 | trans-1233zd + 2-chloropropane | Yes |
| 69 | trans-1233zd + cyclopentane | Yes |
| 70 | trans-1233zd + cyclopentene | Yes |
| 71 | trans-1233zd + methylal | Yes |
| 72 | trans-1233zd + methyl acetate | Yes |
| 73 | trans-1233zd + n-hexane | Yes |
| 74 | trans-1233zd + nitromethane | Yes |
| 75 | cis-1233zd + methanol | Yes |
| 76 | cis-1233zd + ethanol | Yes |
| 77 | cis-1233zd + isopropanol | Yes |
| 78 | cis-1233zd + n-hexane | Yes |
| 79 | cis-1233zd + isohexane | Yes |
| 80 | cis-1233zd + cyclopentane | Yes |
| 81 | cis-1233zd + n-pentane | Yes |
| 82 | cis-1233zd + nitromethane | Yes |
| 83 | cis-1233zd + trans-1,2-DCE | Yes |
| 84 | cis-1233zd + neopentane | Yes |

Example 85

A mixture containing 98% by wt trans-HFO-1233zd and 2% by wt of methanol is prepared, silicone oil is mixed with the blend and the solvent was left to evaporate, a thin coating of silicone oil is left behind in the coupon. This indicated that the solvent blends can be used for silicone oil deposition in various substrates.

Examples 86-111

The steps of Example 85 are generally repeated for Examples 85-111, except that the azeotrope-like mixture identified in the Table below is used instead of trans-HFO-1233zd and methanol.

| Example No. | Azeotrope-like Composition | Oil Deposited |
|---|---|---|
| 86 | trans-1233zd + trans-1,2-DCE | Yes |
| 87 | trans-1233zd + n-pentane | Yes |
| 88 | trans-1233zd + isohexane | Yes |
| 89 | trans-1233zd + neopentane | Yes |
| 90 | trans-1233zd + methanol/n-pentane | Yes |
| 91 | trans-1233zd + methanol/trans-1,2-DCE | Yes |
| 92 | trans-1233zd + ethanol | Yes |
| 93 | trans-1233zd + isopropanol | Yes |
| 94 | trans-1233zd + 1-chloropropane | Yes |
| 95 | trans-1233zd + 2-chloropropane | Yes |
| 96 | trans-1233zd + cyclopentane | Yes |
| 97 | trans-1233zd + cyclopentene | Yes |
| 98 | trans-1233zd + methylal | Yes |
| 99 | trans-1233zd + methyl acetate | Yes |
| 100 | trans-1233zd + n-hexane | Yes |
| 101 | trans-1233zd + nitromethane | Yes |
| 102 | cis-1233zd + methanol | Yes |
| 103 | cis-1233zd + ethanol | Yes |
| 104 | cis-1233zd + isopropanol | Yes |
| 105 | cis-1233zd + n-hexane | Yes |
| 106 | cis-1233zd + isohexane | Yes |
| 107 | cis-1233zd + cyclopentane | Yes |
| 108 | cis-1233zd + n-pentane | Yes |
| 109 | cis-1233zd + nitromethane | Yes |
| 110 | cis-1233zd + trans-1,2-DCE | Yes |
| 111 | cis-1233zd + neopentane | Yes |

Example 112

A mixture containing 98% by wt trans-HFO-1233zd and 2% by wt of methanol is prepared, mineral oil is mixed with the blend. The mineral oil is evenly disbursed throughout the blend. This indicated that the azeotrope-like composition can be used as a solvent.

Examples 113-138

The steps of Example 112 are generally repeated for Examples 113-138, except that the azeotrope-like mixture identified in the Table below is used instead of trans-HFO-1233zd and methanol.

| Example No. | Azeotrope-like Composition | Good Solvency |
|---|---|---|
| 113 | trans-1233zd + trans-1,2-DCE | Yes |
| 114 | trans-1233zd + n-pentane | Yes |
| 115 | trans-1233zd + isohexane | Yes |
| 116 | trans-1233zd + neopentane | Yes |
| 117 | trans-1233zd + methanol/n-pentane | Yes |
| 118 | trans-1233zd + methanol/trans-1,2-DCE | Yes |
| 119 | trans-1233zd + ethanol | Yes |
| 120 | trans-1233zd + isopropanol | Yes |
| 121 | trans-1233zd + 1-chloropropane | Yes |
| 122 | trans-1233zd + 2-chloropropane | Yes |
| 123 | trans-1233zd + cyclopentane | Yes |
| 124 | trans-1233zd + cyclopentene | Yes |
| 125 | trans-1233zd + methylal | Yes |
| 126 | trans-1233zd + methyl acetate | Yes |
| 127 | trans-1233zd + n-hexane | Yes |
| 128 | trans-1233zd + nitromethane | Yes |
| 129 | cis-1233zd + methanol | Yes |
| 130 | cis-1233zd + ethanol | Yes |
| 131 | cis-1233zd + isopropanol | Yes |
| 132 | cis-1233zd + n-hexane | Yes |
| 133 | cis-1233zd + isohexane | Yes |
| 134 | cis-1233zd + cyclopentane | Yes |
| 135 | cis-1233zd + n-pentane | Yes |
| 136 | cis-1233zd + nitromethane | Yes |
| 137 | cis-1233zd + trans-1,2-DCE | Yes |
| 138 | cis-1233zd + neopentane | Yes |

Example 139

An azeotrope-like mixture of about 97 weight percent trans-1233zd and about 3 weight percent trans-1,2-DCE is prepared. This mixture is used as a blowing agent to prepare a closed-cell polyurethane foam and a closed-cell polyisocyanate foam. The cell-gas of the resulting foam is analyzed and is determined to contain at least a portion of the azeotrope-like mixture.

Examples 140-153

The steps of Example 139 are generally repeated for Examples 140-153, except that the azeotrope-like mixture identified in the Table below is used instead of trans-HFO-1233zd and trans-1,2-DCE.

| Example No. | Azeotrope-like Composition | Use as a Blowing Agent Verified | Polyurethane Foam and Polyisocyanate Foam Formed | Cell-gas of foam contains Azeotrope-like Mixture |
|---|---|---|---|---|
| 140 | trans-1233zd + n-pentane | Yes | Yes | Yes |
| 141 | trans-1233zd + isopentane | Yes | Yes | Yes |
| 142 | trans-1233zd + neopentane | Yes | Yes | Yes |
| 143 | trans-1233zd + 1-chloropropane | Yes | Yes | Yes |
| 144 | trans-1233zd + 2-chloropropane | Yes | Yes | Yes |
| 145 | trans-1233zd + cyclopentane | Yes | Yes | Yes |
| 146 | trans-1233zd + cyclopentene | Yes | Yes | Yes |
| 147 | trans-1233zd + methylal | Yes | Yes | Yes |
| 148 | trans-1233zd + methyl acetate | Yes | Yes | Yes |
| 149 | trans-1233zd + water | Yes | Yes | Yes |
| 150 | trans-1233zd + nitromethane | Yes | Yes | Yes |
| 151 | cis-1233zd + cyclopentane | Yes | Yes | Yes |
| 152 | cis-1233zd + n-pentane | Yes | Yes | Yes |
| 153 | cis-1233zd + neopentane | Yes | Yes | Yes |

Example 154

Mixtures were prepared containing 98% by weight trans-HFO-1233zd with about 2 weight percent methanol. Several stainless steel coupons were soiled with mineral oil. Then these coupons were immersed in these solvent blends. The blends removed the oils in a short period of time. The coupons were observed visually and looked clean.

Examples 155-180

The steps of Example 154 are generally repeated for Examples 155-180, except that the azeotrope-like mixture identified in the Table below is used instead of trans-HFO-1233zd and methanol.

| Example No. | Azeotrope-like Composition | Visually Clean |
|---|---|---|
| 155 | trans-1233zd + trans-1,2-DCE | Yes |
| 156 | trans-1233zd + n-pentane | Yes |
| 157 | trans-1233zd + isohexane | Yes |
| 158 | trans-1233zd + neopentane | Yes |
| 159 | trans-1233zd + methanol/n-pentane | Yes |
| 160 | trans-1233zd + methanol/trans-1,2-DCE | Yes |
| 161 | trans-1233zd + ethanol | Yes |
| 162 | trans-1233zd + isopropanol | Yes |
| 163 | trans-1233zd + 1-chloropropane | Yes |
| 164 | trans-1233zd + 2-chloropropane | Yes |
| 165 | trans-1233zd + cyclopentane | Yes |
| 166 | trans-1233zd + cyclopentene | Yes |
| 167 | trans-1233zd + methylal | Yes |
| 168 | trans-1233zd + methyl acetate | Yes |
| 169 | trans-1233zd + n-hexane | Yes |
| 170 | trans-1233zd + nitromethane | Yes |
| 171 | cis-1233zd + methanol | Yes |
| 172 | cis-1233zd + ethanol | Yes |
| 173 | cis-1233zd + isopropanol | Yes |
| 174 | cis-1233zd + n-hexane | Yes |
| 175 | cis-1233zd + isohexane | Yes |
| 176 | cis-1233zd + cyclopentane | Yes |
| 177 | cis-1233zd + n-pentane | Yes |
| 178 | cis-1233zd + nitromethane | Yes |
| 179 | cis-1233zd + trans-1,2-DCE | Yes |
| 180 | cis-1233zd + neopentane | Yes |

Example 181

A solvent blend was prepared containing 98% by wt of trans-HFO-1233zd and 2% by wt of methanol. Kester 1544

Rosin Soldering Flux was placed on stainless steel coupons and heated to approximately 300-400° F., which simulates contact with a wave soldier normally used to solder electronic components in the manufacture of printed circuit boards. The coupons were then dipped in the solvent mixture and removed after 15 seconds without rinsing. Results show that the coupons appeared clean by visual inspection.

Examples 182-207

The steps of Example 181 are generally repeated for Examples 185-207, except that the azeotrope-like mixture identified in the Table below is used instead of trans-HFO-1233zd and methanol.

| Example No. | Azeotrope-like Composition | Visually Clean |
|---|---|---|
| 182 | trans-1233zd + trans-1,2-DCE | Yes |
| 183 | trans-1233zd + n-pentane | Yes |
| 184 | trans-1233zd + isohexane | Yes |
| 185 | trans-1233zd + neopentane | Yes |
| 186 | trans-1233zd + methanol/n-pentane | Yes |
| 187 | trans-1233zd + methanol/trans-1,2-DCE | Yes |
| 188 | trans-1233zd + ethanol | Yes |
| 189 | trans-1233zd + isopropanol | Yes |
| 190 | trans-1233zd + 1-chloropropane | Yes |
| 191 | trans-1233zd + 2-chloropropane | Yes |
| 192 | trans-1233zd + cyclopentane | Yes |
| 193 | trans-1233zd + cyclopentene | Yes |
| 194 | trans-1233zd + methylal | Yes |
| 195 | trans-1233zd + methyl acetate | Yes |
| 196 | trans-1233zd + n-hexane | Yes |
| 197 | trans-1233zd + nitromethane | Yes |
| 198 | cis-1233zd + methanol | Yes |
| 199 | cis-1233zd + ethanol | Yes |
| 200 | cis-1233zd + isopropanol | Yes |
| 201 | cis-1233zd + n-hexane | Yes |
| 202 | cis-1233zd + isohexane | Yes |
| 203 | cis-1233zd + cyclopentane | Yes |
| 204 | cis-1233zd + n-pentane | Yes |
| 205 | cis-1233zd + nitromethane | Yes |
| 206 | cis-1233zd + trans-1,2-DCE | Yes |
| 207 | cis-1233zd + neopentane | Yes |

Having thus described a few particular embodiments of the invention, various alterations, modifications, and improvements will readily occur to those skilled in the art. Such alterations, modifications, and improvements, as are made obvious by this disclosure, are intended to be part of this description though not expressly stated herein, and are intended to be within the spirit and scope of the invention. Accordingly, the foregoing description is by way of example only, and not limiting. The invention is limited only as defined in the following claims and equivalents thereto.

What is claimed is:

1. A binary azeotrope-like mixture consisting essentially of from about 91.6 to about 99.9 weight percent of trans-1-chloro-3,3,3-trifluoropropene and from about 0.1 to about 8.4 weight percent of 1,1,1,3,3-pentafluorobutane.

2. The binary azeotrope-like mixture of claim 1 wherein said azeotrope-like mixture consists essentially of about 92.5 to about 99.9 weight percent trans-1-chloro-3,3,3-trifluoropropene and about 0.1 to about 7.5 weight percent 1,1,1,3,3-pentafluorobutane.

3. The binary azeotrope-like mixture of claim 1 wherein said azeotrope-like mixture consists essentially of about 95 to about 99.9 weight percent trans-1-chloro-3,3,3-trifluoropropene and about 0.1 to about 5 weight percent 1,1,1,3,3-pentafluorobutane.

4. The binary azeotrope-like mixture of claim 1 having a boiling point of 17.5° C.±1.0° C. at ambient pressure.

5. The binary azeotrope-like mixture of claim 1 having a boiling point of between 17.6° C.-18.2° C. at ambient pressure.

6. A blowing agent consisting essentially of the binary azeotrope-like mixture of claim 1.

7. A blowing agent consisting essentially of at least about 5% by weight of the binary azeotrope-like mixture of claim 1.

8. A foamable composition comprising one or more components capable of forming foam and the blowing agent of claim 6.

9. The foamable composition of claim 8 further comprising one or more additives selected from the group consisting of nucleating agents, flame retardants, colorants, processing aids, cross linking gents, and permeability modifiers.

10. A foam formed from the foamable composition of claim 8.

11. The foam of claim 10 comprising a thermoplastic foam.

12. The foam of claim 10 comprising a thermoset foam.

13. A closed cell foam comprising the foam of claim 10.

14. A blowing agent consisting essentially of at least about 15% by weight of the binary azeotrope-like mixture of claim 1.

15. A blowing agent consisting essentially of at least about 50% by weight of the binary azeotrope-like mixture of claim 1.

* * * * *